United States Patent
Hikem et al.

(10) Patent No.: US 11,708,523 B2
(45) Date of Patent: Jul. 25, 2023

(54) METHODS FOR STABILIZING WATER SENSITIVE CLAYS AND MIGRATING FINES IN SUBTERRANEAN FORMATIONS

(71) Applicants: PFP TECHNOLOGY, LLC, Houston, TX (US); ASCEND PERFORMANCE MATERIALS OPERATIONS LLC, Houston, TX (US)

(72) Inventors: Aziz Hikem, Sealy, TX (US); Madhukar Chetty, Houston, TX (US); Derek Vaughn, Houston, TX (US); Prasad Taranekar, Houston, TX (US); Jeffery W. Balko, Annapolis, MD (US)

(73) Assignee: PfP Industries LLC, Houston, TX (US)

( * ) Notice: Subject to any disclaimer, the term of this patent is extended or adjusted under 35 U.S.C. 154(b) by 0 days.

(21) Appl. No.: 17/524,449

(22) Filed: Nov. 11, 2021

(65) Prior Publication Data

US 2022/0169913 A1    Jun. 2, 2022

Related U.S. Application Data

(62) Division of application No. 15/800,424, filed on Nov. 1, 2017, now Pat. No. 11,208,590.

(60) Provisional application No. 62/415,906, filed on Nov. 1, 2016.

(51) Int. Cl.
| | | |
|---|---|---|
| C09K 8/86 | (2006.01) | |
| C09K 8/575 | (2006.01) | |
| C07C 19/01 | (2006.01) | |
| C07C 22/04 | (2006.01) | |
| C07C 55/02 | (2006.01) | |
| C07C 55/22 | (2006.01) | |
| C07C 211/09 | (2006.01) | |
| C07C 211/13 | (2006.01) | |
| C07D 303/08 | (2006.01) | |
| C09K 8/60 | (2006.01) | |

(52) U.S. Cl.
CPC .............. *C09K 8/575* (2013.01); *C07C 19/01* (2013.01); *C07C 22/04* (2013.01); *C07C 55/02* (2013.01); *C07C 55/22* (2013.01); *C07C 211/09* (2013.01); *C07C 211/13* (2013.01); *C07D 303/08* (2013.01); *C09K 8/607* (2013.01); *C09K 8/86* (2013.01); *C09K 2208/12* (2013.01)

(58) Field of Classification Search
CPC .......... C09K 8/575; C09K 8/607; C09K 8/86; C09K 2208/12; C07C 19/01; C07C 22/04; C07C 55/02; C07C 55/22; C07C 211/09; C07C 211/13; C07D 303/08
See application file for complete search history.

(56) References Cited

U.S. PATENT DOCUMENTS

| | | | |
|---|---|---|---|
| 2,873,251 A | 9/1956 | Jones, Jr. | |
| 4,028,055 A * | 6/1977 | Doi .................. | C23F 11/149 |
| | | | 510/264 |
| 4,028,505 A | 6/1977 | Doi et al. | |
| 4,462,718 A | 7/1984 | McLaughlin et al. | |
| 5,558,171 A | 9/1996 | McGlothlin et al. | |
| 6,247,543 B1 | 6/2001 | Patel et al. | |
| 6,436,880 B1 | 8/2002 | Frenier | |
| 7,012,043 B2 | 3/2006 | Klein et al. | |
| 7,087,554 B2 | 8/2006 | Youngson et al. | |
| 7,601,675 B2 | 10/2009 | Poelker et al. | |
| 8,097,567 B2 | 1/2012 | Wilson, Jr. | |
| 9,034,801 B2 | 5/2015 | Merli et al. | |
| 2000/6289164 | 12/2006 | Smith et al. | |
| 2012/0295820 A1 * | 11/2012 | Falana .................. | C09K 8/68 |
| | | | 507/239 |
| 2013/0213657 A1 | 8/2013 | Dobson, Jr. et al. | |
| 2014/0116710 A1 | 5/2014 | Naser-El-Din et al. | |
| 2015/0299554 A1 | 10/2015 | Pakulski et al. | |
| 2015/0344767 A1 | 12/2015 | Lei et al. | |
| 2015/0353807 A1 | 12/2015 | Witham et al. | |
| 2017/0247595 A1 | 8/2017 | Cliffe | |

FOREIGN PATENT DOCUMENTS

| | | | |
|---|---|---|---|
| WO | 2013124003 A1 | 8/2013 | |
| WO | 2014191389 A1 | 12/2014 | |
| WO | 2015191027 A1 | 12/2015 | |

OTHER PUBLICATIONS

Zhong, H., et al, "Bis(hexamethylene)triamine as potential shale inhibitor in waterbased drilling fluid," Open Petroleum Engineering Journal (2013) 6:4956. http://benthamopen.com/contents/pdf/TOPEJ/TOPEJ649.pdf Bis(hexamethylene)triamine was introduced as a potential shale inhibitor in water based drilling fluid. The inhibitive properties were evaluated through bentonite inhibition test, cuttings hot rolling dispersion test and particle distribution measurement.

Hudson, E.H., et al., "Survey of polyamines as prospective shale stabilizers," American Association of Drilling Engineers AADE Fluids Technical Conference and Exhibition, 1213 Apr. 2016; AADE 16FTCE56. http://www.newpark.com/internet/documents/NDF%20USA%20Resource%20Library/AADE16FTCE56%20%20Hudson.pdf Polyamines are used in high performance water based drilling fluids for their ability to stabilize clays when drilling through watersensitive shales.

(Continued)

*Primary Examiner* — Kumar R Bhushan

(74) *Attorney, Agent, or Firm* — Robert W. Strozier

(57) ABSTRACT

Clay stabilization compositions include one or a plurality of triamino compounds and/or derivatives thereof, fluids containing an effective amount of the clay stabilization compositions and methods for making and using same.

18 Claims, No Drawings

(56) References Cited

OTHER PUBLICATIONS

Karpinski, B., et al., "Clay Minerals; Mineralogy and Phenomenon of Clay Swelling in Oil & Gas Industry," Advances in Materials Science (Mar. 2015) 15(1):3755. http://www.degruyter.com/downloadpdf/j/adms.2015.15.issue1/adms20150006/adms20150006.xml In drilling, a phenomenon of swelling clays is frequently observed. This paper presents review literature on mineralogy of clay minerals and phenomenon of swelling in oil and gas industry. Unique on exchange properties and clay swelling mechanisms are also considered.

\* cited by examiner

METHODS FOR STABILIZING WATER SENSITIVE CLAYS AND MIGRATING FINES IN SUBTERRANEAN FORMATIONS

RELATED APPLICATIONS

This application is a divisional of U.S. patent application Ser. No. 15/800,424 filed Nov. 1, 2017 (1 Nov. 2017), which claims the benefit of and priority to U.S. Provisional Patent Application Ser. No. 62/415,906 filed Nov. 1, 2016 (1 Nov. 2016).

BACKGROUND OF THE INVENTION

1. Field of the Invention

Embodiments of the present disclosure relates to clay stabilization compositions and methods for making and using same.

More particularly, embodiments of the present disclosure relates to clay stabilization compositions and methods for making and using same, where the compositions include derivatized polyamine and where the polyamines are non-polymeric.

2. Description of the Related Art

Swelling clays and migrating fines are a frequent cause of formation damage. When fresh water is introduced to a formation that contains natural brine, swelling clays and migrating fines can bridge off capillaries and block the movement of fluids to the wellbore. This loss of permeability can seriously impair the recovery of hydrocarbons from the well. Additionally, clays and fines can be brought to the wellbore during production and lead to abrasion damage of pumping equipment.

A variety of methods for inhibiting the swelling of clays and migration of fines have been devised. Brine slugs have been used prior to the introduction of drilling or stimulation fluids. The most common method is to add organic or inorganic salts to drilling and/or stimulation fluids in order to stabilize the clays. For many years, the most commonly used salt was potassium chloride. The K$^+$ cation undergoes an ion exchange with the Na$^+$ cation on the clay, converting it to a non-swelling form. In recent years, quaternized organic salts such as tetramethylammonium chloride (TMAC) and choline chloride have been used with success. Together, these low molecular weight salts are considered to be temporary clay stabilizers because the single ionic bond they form with the clay make them susceptible to a reverse ion exchange with Na$^+$ when the well is put into production. This converts the clay from the non-swelling form back to the swelling form.

Polymers have been used to address the problem of temporary clay stabilizers. Multiple cationic sites along a polymer chain means a greater charge density, and more sites for the polymer to bond to the clay. These clay stabilizing polymers are known as permanent clay stabilizers. While cationic polymers used for clay stabilization are effective and long-lasting, the high molecular weight of most polymers means that they can become problematic in tight or low porosity wells. The polymers can plate out on the rock face, thereby blocking flow through the capillaries.

Thus, there is a need in the art for non-polymeric clay stabilization compositions for use in treating subterranean formations.

SUMMARY OF THE INVENTION

Embodiments of the present disclosure provide compositions for stabilizing water sensitive clays and migrating fines in subterranean formations, where the compositions include one or more compounds of the general Formulas I and II:

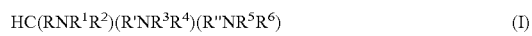

$$HC(RNR^1R^2)(R'NR^3R^4)(R''NR^5R^6) \qquad (I)$$

$$HC(RNR^1R^2R^7)(R'NR^3R^4R^8)(R''NR^5R^6R^9)X_n \qquad (II)$$

where the R, R', and R" groups are the same or different that are hydrocarbyl linking groups having between 1 and 8 carbon atoms, when the R, R', and R" groups include 2 to 8 carbon atoms, then one or more carbon atoms may be replaced by oxygen atoms, acetate groups, or carbonyl groups, where the R$^{1-6}$ groups are the same or different and are hydrogen atoms or hydrocarbyl groups including from 1 to 6 carbon atoms, when the R$^{1-6}$ groups include 2 to 6 carbon atoms, then one or more carbon atoms may be replaced by oxygen atoms, acetate groups, or carbonyl groups, where the R$^{7-9}$ groups are the same or different and are absent, a hydrogen atom, and/or a hydrocarbyl group including from 1 to 6 carbon atoms; provided, however, that at least one of the R$^{7-9}$ groups is a hydrogen atom or a hydrocarbyl group, when the R$^{7-9}$ groups include 2 to 6 carbon atoms, then one or more carbon atoms may be replaced by oxygen atoms, acetate groups, or carbonyl groups, and where X groups are the same or different and each of the X groups is a halide ion, a formate ion, an acetate ion, a phosphate ion, a fumarate ion, a sulfate ion, a hydrogensulfate ion, alkylsulfate ion, a citrate ion, an oxalate ion, or mixtures thereof, and where n is an integer having a value between 1 and 3.

Embodiments of the present disclosure provide methods for preparing the compounds of formula I, where at least one R$^{1-6}$ groups is a hydrocarbyl group, and compounds of Formula II. Compounds of Formula I, where at least one R$^{1-6}$ groups is a hydrocarbyl group, are prepared by reacting a compound of Formula I, where all of the R$^{1-6}$ groups are hydrogen atoms, with an alkylating agent to achieve the desired number of alkylations. Compounds of Formula II are prepared by reacting compounds of Formula I with an HX or R$^7$X, R$^8$X, or R$^9$X under conditions to form a desired compound of Formula II.

Embodiments of the present disclosure provide methods for treating a formation or zone of a formation with a composition including an effective amount of one or a plurality of compounds of Formulas I and II, where the effective amount is sufficient to stabilize a clay containing formation and reduce migrating fines.

DEFINITIONS OF TERM USED IN THE INVENTION

The following definitions are provided in order to aid those skilled in the art in understanding the detailed description of the present invention.

The term "about" means that the value is within about 10% of the indicated value. In certain embodiments, the value is within about 5% of the indicated value. In certain embodiments, the value is within about 2.5% of the indicated value. In certain embodiments, the value is within about 1% of the indicated value. In certain embodiments, the value is within about 0.5% of the indicated value.

The term "substantially" means that the value is within about 5% of the indicated value. In certain embodiments, the value is within about 2.5% of the indicated value. In certain embodiments, the value is within about 10% of the indicated value. In certain embodiments, the value is within about 0.5% of the indicated value. In certain embodiments, the value is within about 0.1% of the indicated value.

The term "fracturing fluids" refers to any fluid that is used in fracturing operations for oil and/or gas wells, geo-thermal wells, water wells, injections wells, or other similar wells.

The term "drilling fluids" refers to any fluid that is used during well drilling operations including oil and/or gas wells, geo-thermal wells, water wells or other similar wells.

The term "over-balanced drilling fluid" means a drilling fluid having a circulating hydrostatic density (pressure) that is greater than the formation density (pressure).

The term "under-balanced and/or managed pressure drilling fluid" means a drilling fluid having a circulating hydrostatic density (pressure) lower or equal to a formation density (pressure). For example, if a known formation at 10,000 ft (True Vertical Depth—TVD) has a hydrostatic pressure of 5,000 psi or 9.6 lbm/gal, an under-balanced drilling fluid would have a hydrostatic pressure less than or equal to 9.6 lbm/gal. Most under-balanced and/or managed pressure drilling fluids include at least a density reduction additive. Other additives may be included such as corrosion inhibitors, pH modifiers and/or a shale inhibitors.

The term "gpt" means gallons per thousand gallons.
The term "ppt" means pounds per thousand gallons.
The term "ppg" means pounds per gallon.
The term "mL" means milliliter.
The term "L" means liter.
The terms "wt. %" or "w/w" means weight percent.
The terms "vol. %" or "v/v" means volume percent.
The term "w/v" means weight per volume.
The term "v/w" means volume per weight.

DETAILED DESCRIPTION OF THE INVENTION

The inventor has found that an ideal solution to the problem of clay stabilization is a molecule that contains multiple cationic sites for stronger bonding to the clay, but is non-polymeric so that it does not constrict fluid movement through the formation. Triaminononane (TAN), 4-aminomethyl-1,8-octanediamine, is a tri-functional primary amine that may be derivatized to form alkylated and quaternized products. The increased charge density of the derivatized molecule allows it to bind more strongly to swelling clays, while its relatively low molecular weight allow it to stabilize the clay permanently without causing formation damage by blocking pore throats and reducing permeability.

The clay stabilizers of the present disclosure are permanent but possess a low molecular weight and include where the compositions include one or more compounds of the general Formulas I and II:

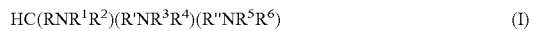

where the R, R', and R" groups are the same or different that are hydrocarbyl linking groups having between 1 and 8 carbon atoms, when the R, R', and R" groups include 2 to 8 carbon atoms, then one or more carbon atoms may be replaced by oxygen atoms, acetate groups, or carbonyl groups, where the $R^{1-6}$ groups are the same or different and are hydrogen atoms or hydrocarbyl groups including from 1 to 6 carbon atoms, when the $R^{1-6}$ groups include 2 to 6 carbon atoms, then one or more carbon atoms may be replaced by oxygen atoms, acetate groups, or carbonyl groups, where the $R^{7-9}$ groups are the same or different and are absent, a hydrogen atom, or a hydrocarbyl group including from 1 to 6 carbon atoms; provided, however, that at least one of the $R^{7-9}$ groups is a hydrogen atom or a hydrocarbyl group, when the $R^{7-9}$ groups include 2 to 6 carbon atoms, then one or more carbon atoms may be replaced by oxygen atoms, acetate groups, or carbonyl groups, and where the X groups are the same or different and each of the X groups is a halide ion, a formate ion, an acetate ion, a phosphate ion, a fumarate ion, a sulfate ion, a hydrogensulfate ion, alkylsulfate ion, a citrate ion, an oxalate ion, or mixtures thereof, and where n is an integer having a value between 1 and 3. In certain embodiments, the R, R', and R" groups are the same or different and are linear alkyl linking groups having between 1 and 8 carbon atoms of the formula $-(CH_2)_m-$, where m is an integer having a value between 2 and 8. In other embodiments, the R group is a linear alkyl group having between 1 and 3 carbon atoms, the R' group is linear alkyl group having between 2 and 4 carbon atoms, and the R" group is linear alkyl linking groups having between 3 and 5 carbon atoms.

In other embodiments, the clay stabilizer compositions include one or more derivatized compounds of triaminonone (TAN)(4-aminomethyl-1,8-octanediamine). TAN is a tri-functional primary amine of Formula III:

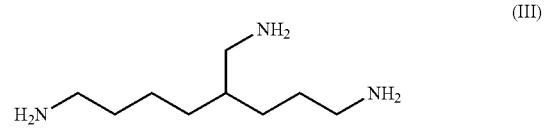 [SMILES: NCCCCC(CN)CCCN]

In other embodiments, the clay stabilizer compositions include one or more quaternary amines of Formula IV:

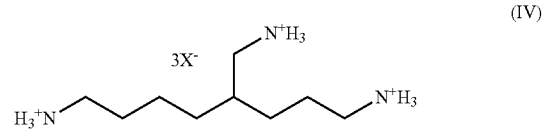

where $X^-$ is as defined above. These salts are analogous to the more commonly used clay stabilizing salts (e.g., potassium chloride, tetramethylammonium chloride, choline chloride, etc.), but differ in that the tri-functionality of TAN allows these quaternized compounds to bind more strongly to swelling clays.

In other embodiments, the clay stabilizer compositions include one or more alkylated TANs of Formula V such as methylated TANs:

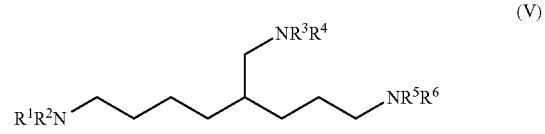

followed by quaternization using strong acids to form compounds of Formula VI:

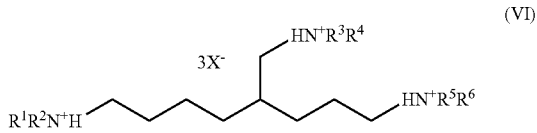

or followed by quaternization using strong alkylating agents to form compounds of Formula VII:

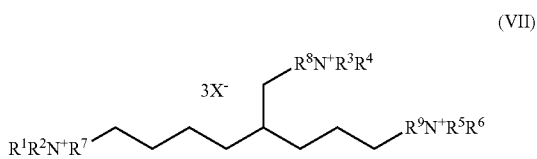

where the $R^{1-6}$ groups, the $R^{7-9}$ groups, the X groups, and n are as set forth above.

Suitable Reagents

Amines, Alkanol Amines, and Alkylene Ether Amines

Suitable amines for use in the disclosure include, without limitation, 3-aminomethyl-1,6-hexanediamine, 3-aminoethyl-1,6-hexanediamine, 3-aminomethyl-1,7-heptanediamine, 3-aminoethyl-1,7-heptanediamine, 3-aminopropyl-1,7-hexanediamine, 4-aminomethyl-1,8-octanediamine (triaminononane (TAN)), 4-aminoethyl-1,8-octanediamine, 4-aminopropyl-1,8-octanediamine, 4-aminomethyl-1,9-noanediamine, 4-aminoethyl-1,9-nonanediamine, 4-aminopropyl-1,9-nonanediamine, 4-aminomethyl-1,10-decanediamine, 4-aminoethyl-1,10-decanediamine, 4-aminopropyl-1,10-decanediamine, 4-aminobutyl-1,10-decanediamine, 3-dimethylaminomethyl-1,6-hexanedimethylamine, 3-dimethylaminoethyl-1,6-hexanedimethylamine, 3-dimethylaminomethyl-1,7-heptanedimethylamine, 3-dimethylaminoethyl-1,7-heptanedimethylamine, 3-dimethylaminopropyl-1,7-hexanedimethylamine, 4-dimethylaminomethyl-1,8-octanedimethylamine, 4-dimethylaminoethyl-1,8-octanedimethylamine, 4-dimethylaminopropyl-1,8-octanedimethylamine, 4-dimethylaminomethyl-1,9-noanedimethylamine, 4-dimethylaminoethyl-1,9-nonanedimethylamine, 4-dimethylaminopropyl-1,9-nonanedimethylamine, 4-dimethylaminomethyl-1,10-decanedimethylamine, 4-dimethylaminoethyl-1,10-decanedimethylamine, 4-dimethylaminopropyl-1,10-decanedimethylamine, 4-dimethylaminobutyl-1,10-decanedimethylamine,3-diethylaminomethyl-1,6-hexanediethylamine, 3-diethylaminoethyl-1,6-hexanediethylamine, 3-diethylaminomethyl-1,7-heptanediethylamine, 3-diethylaminoethyl-1,7-heptanediethylamine, 3-diethylaminopropyl-1,7-hexanediethylamine, 4-diethylaminomethyl-1,8-octanediethylamine, 4-diethylaminoethyl-1,8-octanediethylamine, 4-diethylaminopropyl-1,8-octanediethylamine, 4-diethylaminomethyl-1,9-noanediethylamine, 4-diethylaminoethyl-1,9-nonanediethylamine, 4-diethylaminopropyl-1,9-nonanediethylamine, 4-diethylaminomethyl-1,10-decanediethylamine, 4-diethylaminoethyl-1,10-decanediethylamine, 4-diethylaminopropyl-1,10-decanediethylamine, 4-diethylaminobutyl-1,10-decanediethylamine, 3-methylethylaminomethyl-1,6-hexanemethylethylamine, 3-methylethylaminoethyl-1,6-hexanemethylethylamine, 3-methylethylaminomethyl-1,7-heptanemethylethylamine, 3-methylethylaminoethyl-1,7-heptanemethylethylamine, 3-methylethylaminopropyl-1,7-hexanemethylethylamine, 4-methylethylaminomethyl-1,8-octanemethylethylamine, 4-methylethylaminoethyl-1,8-octanemethylethylamine, 4-methylethylaminopropyl-1,8-octanemethylethylamine, 4-methylethylaminomethyl-1,9-noanemethylethylamine, 4-methylethylaminoethyl-1,9-nonanemethylethylamine, 4-methylethylaminopropyl-1,9-nonanemethylethylamine, 4-methylethylaminomethyl-1,10-decanemethylethylamine, 4-methylethylaminoethyl-1,10-decanemethylethylamine, 4-methylethylaminopropyl-1,10-decanemethylethylamine, 4-methylethylaminobutyl-1,10-decanemethylethylamine, other dialkylated amines, quaternized derivatives thereof, and mixtures or combinations thereof.

Suitable quaternizing agents for forming the X counterions include, without limitation, compounds of the general formula HX, $R^7X$, $R^8X$, $R^9X$, $R^{16}X$, $R^{17}X$, and $R^{18}X$ including, without limitation, dialkylsulfates, where the alkyl groups are the same or different and have between 1 and 6 carbon atoms, chloroalkylbenzenes such as benzylchloride, 1,4-chloromethylbenzene, etc., where the alkyl group has between 1 and 6 carbon atoms, alkylchlorides, where the alkyl group has between 1 and 24 carbon atoms, chloroethers, where the alkyl group has between 4 and 24 carbon atoms, and alkylsulfonates, where the alkyl group is a straight chain alkyl group, or branched alkyl group, or cyclic alkyl group has between 1 to 24 carbon atoms and/or mixtures or combinations thereof. In all of these compounds one or more of carbon atoms may be replaced by oxygen atoms, acetate groups, or carbonyl groups. Exemplary examples of dialkylsulfate compounds include, without limitation, dimethylsulfate, methylethylsulfate, diethylsulfate, dipropylsulfate, methylpropylsulfate, ethylpropylsulfate, higher dialkyl sulfates and mixed dialkyl sulfates, or mixtures and combinations thereof. Exemplary examples of chloroalkylbenzenes include, without limitation, benzyl chloride, chloroxylene, chloroethylbenzene, chloropropylbenzene, chlorobutylbenzene, higher chloroalkylbenzenes, or mixtures and combinations thereof. Exemplary examples of alkylchlorides include, without limitation, methyl chloride, ethyl chloride, propyl chloride, butyl chloride, pentyl chloride, hexyl chloride, heptyl chloride, octyl chloride,1-chlorohexadecane, higher alkyl chloride, or mixtures and combinations. Exemplary examples of chloroethers include, without limitation, chloroethylethanolether, dichloroethylether, higher chlorinated ethers, or mixtures and combinations. Exemplary examples of alkylsulfonates are methylsulfonate, ethane sulfonic acid, 1-butane sulfonic acid, petroleum sulfonic acids, benzenesulfonic acid, toluene sulfonic acid, dedecylbenzene sulfonic acid, and mixtures or combination thereof.

Aqueous Based Fluids

Suitable aqueous base fluids for use in this invention includes, without limitation, freshwater, production water, seawater other sodium brines, non-sodium brines (phosphate, sulfate, nitrate, etc.), aqueous makeup systems, and mixture or combinations thereof.

Organic Base Fluids

Suitable oil based fluids for use in this invention includes, without limitation, synthetic hydrocarbon fluids, petroleum based hydrocarbon fluids, natural hydrocarbon (non-aqueous) fluids or other similar hydrocarbons or mixtures or combinations thereof. The hydrocarbon fluids for use in the present invention have viscosities ranging from about $5\times10^{-6}$ to about $600\times10^{-6}$ m$^2$/s (5 to about 600 centistokes). Exemplary examples of such hydrocarbon fluids include, without limitation, polyalphaolefins, polybutenes, polyesters, vegetable oils, animal oils, other essential oil, diesel having a low or high sulfur content, kerosene, jet-fuel, internal olefins (IO) having between about 12 and 20 carbon atoms, linear alpha olefins having between about 14 and 20 carbon atoms, polyalpha olefins having between about 12 and about 20 carbon atoms, isomerized alpha olefins (IAO) having between about 12 and about 20 carbon atoms, VM&P Napta, Limpar, Linear paraffins, detergent alkylates and Parafins having between 13 and about 16 carbon atoms, and mixtures or combinations thereof.

Suitable polyalphaolefins (PAOs) include, without limitation, polyethylenes, polypropylenes, polybutenes, polypentenes, polyhexenes, polyheptenes, higher PAOs, copolymers thereof, and mixtures thereof. Exemplary examples of PAOs include PAOs sold by Mobil Chemical Company as SHF fluids and PAOs sold formerly by Ethyl Corporation under the name ETHYLFLO and currently by Albemarle Corporation under the trade name Durasyn. Such fluids include those specified as ETYHLFLO 162, 164, 166, 168, 170, 174, and 180. Well suited PAOs for use in this invention include blends of about 56% of ETHYLFLO now Durasyn 174 and about 44% of ETHYLFLO now Durasyn 168.

Exemplary examples of polybutenes include, without limitation, those sold by Amoco Chemical Company and Exxon Chemical Company under the trade names INDOPOL and PARAPOL, respectively. Well suited polybutenes for use in this invention include Amoco's INDOPOL 100.

Exemplary examples of polyolester include, without limitation, neopentyl glycols, trimethylolpropanes, pentaerythriols, dipentaerythritols, and diesters such as dioctylsebacate (DOS), diactylazelate (DOZ), and dioctyladipate.

Exemplary examples of petroleum based fluids include, without limitation, white mineral oils, paraffinic oils, and medium-viscosity-index (MVI) naphthenic oils having viscosities ranging from about $5\times10^{-6}$ to about $600\times10^{-6}$ m$^2$/s (5 to about 600 centistokes) at 40° C. Exemplary examples of white mineral oils include those sold by Witco Corporation, Arco Chemical Company, PSI, and Penreco. Exemplary examples of paraffinic oils include solvent neutral oils available from Exxon Chemical Company, high-viscosity-index (HVI) neutral oils available from Shell Chemical Company, and solvent treated neutral oils available from Arco Chemical Company. Exemplary examples of MVI naphthenic oils include solvent extracted coastal pale oils available from Exxon Chemical Company, MVI extracted/acid treated oils available from Shell Chemical Company, and naphthenic oils sold under the names HydroCal and Calsol by Calumet.

Exemplary examples of vegetable oils include, without limitation, castor oils, corn oil, olive oil, sunflower oil, sesame oil, peanut oil, other vegetable oils, modified vegetable oils such as cross linked castor oils and the like, and mixtures thereof. Exemplary examples of animal oils include, without limitation, tallow, mink oil, lard, other animal oils, and mixtures thereof. Other essential oils will work as well. Of course, mixtures of all the above identified oils can be used as well.

Suitable base fluid compositions or solvent systems of this invention include, without limitation, blends of biodegradable, non-toxic, non-hazardous solvents including biodegradable paraffins, isoparaffins, olefins, naphthenes, esters, and oxygenates having a flashpoint ≥80° C. and a pour point of about 19° F. Exemplary examples include HF-1000™, ODC®, LPA®, terpenes and mixture of terpenes derived from citrus plants including d-limonenes, orange terpenes, lemon terpenes, grapefruit terpenes, orange oil, lemon oil, other citrus terpenes, other citrus oils, blends of HF-1000™, ODC®, and/or LPA® with the terpenes and mixtures of terpenes or mixtures and combinations thereof.

Synthetic Hydratable Polymers

Suitable synthetic hydratable polymers include, without limitation, (a) high molecular weight homo- and/or copolymers of acrylic acid crosslinked with polyalkenyl polyethers, (b) high molecular weight hydrophobically modified, cross-linked polyacrylate polymers, (c)hydrophilic, anionic, high molecular weight, cross-linked polyacrylic acid polymers, and (d) mixtures or combinations thereof.

In certain embodiments, the cross-linked polyacrylate polymer used in this invention have a minimum Brookfield RVF or RVT Viscosity, (mPa·s) (20 rpm at 25° C., neutralized solutions) of 19,000 and a maximum viscosity of 35,000 for a 0.2 wt. % solution. In other embodiments, the cross-linked polyacrylate polymer used in this invention have a minimum viscosity of 40,000 and a maximum viscosity of 60,000 for a 0.5 wt. % solution. In other embodiments, the cross-linked polyacrylate polymer used in this invention have a minimum viscosity of 45,000 and a maximum viscosity of 80,000 for a 1.0 wt. % solution. In other embodiments, the cross-linked polyacrylate polymer used in this invention have a minimum Brookfield RVF or RVT Viscosity, (mPa·s) (20 rpm at 25° C., neutralized solutions) of 13,000 and a maximum viscosity of 30,000 for a 0.2 wt. % solution. In other embodiments, the cross-linked polyacrylate polymer used in this invention have a minimum viscosity of 40,000 and a maximum viscosity of 60,000 for a 0.5 wt. % solution. In certain embodiments, the cross hydrophobically modified, crosslinked polyacrylate polymer used in this invention have a minimum Brookfield RVT viscosity (mPa·s) (20 rpm @ 25° C., spindle #7) of 47,000 and a maximum viscosity of 67,000 for a 1.0 wt % solution neutralized to a pH between 6.0 and 6.3. In other embodiments, the hydrophobically modified crosslinked polyacrylate polymer used in this invention have a minimum Brookfield RVT viscosity (mPa·s) (20 rpm @ 25° C., spindle #7) of 45,000 and a maximum viscosity of 65,000 for a 0.5 wt % solution neutralized to a pH between 6.0 and 6.3. In other embodiments, the crosslinked acrylic acid homopolymer used in this invention have a minimum Brookfield RVT viscosity (mPa·s) (20 rpm @ 25° C., spindle #7) of 50,000 and a maximum viscosity of 70,000 for a 0.5 wt % solution neutralized to a pH between 6.0 and 6.3.

Exemplary synthetic rheology modifiers include acrylic based polymers and copolymers. One class of acrylic based rheology modifiers are the carboxyl functional alkali-swellable and alkali-soluble thickeners (ASTs) produced by the free-radical polymerization of acrylic acid alone or in combination with other ethylenically unsaturated monomers. The polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and $C_1$-$C_{30}$ alkyl esters of acrylic acid and methacrylic acid. Optionally, other ethylenically unsaturated monomers such as, for example, styrene, vinyl acetate, ethylene, butadiene, acrylonitrile, as well as mixtures thereof can be copolymerized into the backbone. The foregoing polymers are crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from but not limited to allyl ethers of sucrose and allyl ethers of pentaerythritol, and mixtures thereof. These polymers are more fully described in U.S. Pat. Nos. 5,087,445; 4,509,949; and 2,798,053.

In one aspect, the AST rheology modifier or thickener is a crosslinked homopolymer polymerized from acrylic acid or methacrylic acid and is generally referred to under the INCI name of Carbomer. Commercially available Carbomers include Carbopol® polymers 934, 940, 941, 956, 980, and 996 available from Lubrizol Advanced Materials, Inc.

In a further aspect, the rheology modifier is selected from a crosslinked copolymer polymerized from a first monomer selected from one or more monomers of acrylic acid, methacrylic acid and a second monomer selected from one or more $C_{10}$-$C_{30}$ alkyl acrylate esters of acrylic acid or methacrylic acid. In one aspect, the monomers can be polymerized in the presence of a steric stabilizer such as disclosed in U.S. Pat. No. 5,288,814 which is herein incorporated by reference. Some of the forgoing polymers are designated under INCI nomenclature as Acrylates/C10-30 Alkyl Acrylate Crosspolymer and are commercially available under the trade names Carbopol® 1342 and 1382, Carbopol® Ultrez 20 and 21, Carbopol® ETD 2020, and Pemulen® TR-1 and TR-2 from Lubrizol Advanced Materials, Inc. Other acrylic copolymer rheology modifiers marketed by Lubrizol Advanced Materials, Inc. are available under the Carbopol® EZ series trade name.

The crosslinked carboxyl group containing homopolymers and copolymers of the invention have weight average molecular weights ranging from at least 1 million to billions of Daltons in one aspect and from about 1.5 to about 4.5 billion Daltons in another aspect (see TDS-222, Oct. 15, 2007, Lubrizol Advanced Materials, Inc., which is herein incorporated by reference).

Exemplary examples of suitable synthetic hydratable polymers include, without, limitation, CARBOPOL® Aqua SF-1 Polymer (acrylates copolymer), CARBOPOL® Aqua SF-2 Polymer (acrylates crosspolymer-4), CARBOPOL® Aqua CC Polymer (polyacrylate-1 crosspolymer), CARBOPOL® 934 Polymer (carbomer), CARBOPOL® 940 Polymer (carbomer), CARBOPOL® 941 Polymer (carbomer), CARBOPOL® 980 Polymer (carbomer), CARBOPOL® 981 Polymer (carbomer), CARBOPOL® 1342 Polymer (acrylates/$C_{10-30}$ alkyl acrylate crosspolymer), CARBOPOL® 1382 Polymer (acrylates/$C_{10-30}$ alkyl acrylate crosspolymer), CARBOPOL® 2984 Polymer (carbomer), CARBOPOL® 5984 Polymer (carbomer), CARBOPOL® Ultrez 10 Polymer (carbomer), CARBOPOL® Ultrez 20 Polymer (acrylates/$C_{10-30}$ alkyl acrylate crosspolymer), CARBOPOL® Ultrez 21 Polymer (acrylates/$C_{10-30}$ alkyl acrylate crosspolymer), CARBOPOL® Ultrez 30 Polymer (carbomer), CARBOPOL® ETD 2020 Polymer (acrylates/$C_{10-30}$ alkyl acrylate crosspolymer), CARBOPOL® ETD 2050 Polymer (carbomer), CARBOPOL® 674 Polymer, CARBOPOL® 676 Polymer, CARBOPOL® 690 Polymer, CARBOPOL® ETD 2623 Polymer, CARBOPOL® ETD 2691 Polymer, CARBOPOL® EZ-2 Polymer, CARBOPOL® EZ-3 Polymer, CARBOPOL® EZ-4 Polymer, CARBOPOL® Aqua 30 Polymer, and mixtures or combinations thereof, where these polymers are available from The Lubrizol Corporation and Ashland™ 941 CARBOMER, Ashland™ 981 CARBOMER, Ashland™ 980 CARBOMER (acrylic acid polymer), Ashland™ 940 CARBOMER, and mixtures or combinations thereof, where these polymers are available from Ashland Inc and Lubrizol Corporation.

Natural Hydratable Polymers

Suitable natural hydratable water soluble polymers for use in fracturing fluids of this invention include, without limitation, polysaccharides and mixtures or combinations thereof. Suitable polysaccharides include galactomannan gum and cellulose derivatives. In certain embodiments, the polysaccharides include guar gum, locust bean gum, carboxymethylguar, hydroxyethylguar, hydroxypropylguar, carboxymethylhydroxypropylguar, carboxymethylhydroxyethylguar, hydroxymethyl cellulose, carboxymethylhydroxyethyl cellulose, and hydroxyethyl cellulose and mixtures or combinations thereof.

The natural hydratable polymer useful in the present invention can be any of the hydratable polysaccharides having galactose or mannose monosaccharide components and are familiar to those in the well service industry. These polysaccharides are capable of gelling in the presence of a crosslinking agent to form a gelled based fluid. For instance, suitable hydratable polysaccharides are the galactomannan gums, guars and derivatized guars. Specific examples are guar gum and guar gum derivatives. Suitable gelling agents are guar gum, hydroxypropyl guar and carboxymethyl hydroxypropyl guar. In certain embodiment, the hydratable polymers for the present invention are guar gum and carboxymethyl hydroxypropyl guar and hydroxypropyl guar. Other exemplary fracturing fluid formulations are disclosed in U.S. Pat. Nos. 5,201,370 and 6,138,760, which are incorporated herein by reference.

Proppants

The proppant type can be sand, intermediate strength ceramic proppants (available from Carbo Ceramics, Norton Proppants, etc.), sintered bauxites and other materials known to the industry. Any of these base propping agents can further be coated with a resin (available from Santrol, a Division of Fairmount Industries, Borden Chemical, etc.) to potentially improve the clustering ability of the proppant. In addition, the proppant can be coated with resin or a proppant flowback control agent such as fibers for instance can be simultaneously pumped. By selecting proppants having a contrast in one of such properties such as density, size and concentrations, different settling rates will be achieved.

Propping agents or proppants are typically added to the fracturing fluid prior to the addition of a crosslinking agent. However, proppants may be introduced in any manner which achieves the desired result. Any proppant may be used in embodiments of the invention. Examples of suitable proppants include, but are not limited to, quartz sand grains, glass and ceramic beads, walnut shell fragments, aluminum pellets, nylon pellets, and the like. Proppants are typically used in concentrations between about 1 to 8 lbs. per gallon of a fracturing fluid, although higher or lower concentrations may also be used as desired. The fracturing fluid may also contain other additives, such as surfactants, corrosion inhibitors, mutual solvents, stabilizers, paraffin inhibitors, tracers to monitor fluid flow back, and so on.

Besides the proppant concentrations in the final formulation, the particles sizes of the proppants are also a factor in the performance of the fluids of this invention. In certain embodiments, the proppants have sizes of 16/20 mesh, 16/30 mesh, 20/40 mesh and mixtures and combinations thereof. In addition, proppant density is another factor in the performance of the fluids of this invention. Exemplary examples of the proppants useful in this invention include, without limitation, CARBO-HSP® 16/30 mesh and 20/40 mesh having a bulk density=2 g/cm$^3$ and CARBO-LITE® 16/20 mesh and 20/40 mesh having a bulk density=1.57 g/cm$^3$, and mixtures or combinations thereof.

Cross-Linking Agents

Suitable cross-linking agent for use in this invention when the compositions include minor amount of natural hydratatable polymers include, without limitation, any suitable cross-linking agent for use with the gelling agents. Exemplary cross-linking agents include, without limitation, di- and tri-valent metal salts such as calcium salts, magnesium salts, barium salts, copperous salts, cupric salts, ferric salts, aluminum salts, or mixtures or combinations thereof.

A suitable crosslinking agent can be any compound that increases the viscosity of the fluid by chemical crosslinking, physical crosslinking, or any other mechanisms. For example, the gellation of a hydratable polymer can be achieved by crosslinking the polymer with metal ions including boron in combination with zirconium, and titanium containing compounds. The amount of the crosslinking agent used also depends upon the well conditions and the type of treatment to be effected, but is generally in the range of from about 0.001 wt. % to about 2 wt. % of metal ion of the crosslinking agent in the hydratable polymer fluid. In some applications, the aqueous polymer solution is cross-linked immediately upon addition of the crosslinking agent to form a highly viscous gel. In other applications, the reaction of the crosslinking agent can be retarded so that viscous gel formation does not occur until the desired time.

When the synthetic hydratable compositions of this invention include no or substantially no natural hydratable polymers, then viscosity may be increased solely by the addition of a sufficient amount of an aqueous alkali solution to the compositions. When pH goes up to about pH 6 to about pH 10, the viscosity is increased due to the ionization of carboxylic acid group and the formation of ionic interactions with metal ions.

The boron based crosslinking agents may be selected from the group consisting of boric acid, sodium tetraborate, and mixtures thereof. These are described in U.S. Pat. No. 4,514,309. In some embodiments, the well treatment fluid composition may further comprise a proppant.

Breakers

The term "breaking agent" or "breaker" refers to any chemical that is capable of reducing the viscosity of a gelled fluid. As described above, after a fracturing fluid is formed and pumped into a subterranean formation, it is generally desirable to convert the highly viscous gel to a lower viscosity fluid. This allows the fluid to be easily and effectively removed from the formation and to allow desired material, such as oil or gas, to flow into the well bore. This reduction in viscosity of the treating fluid is commonly referred to as "breaking". Consequently, the chemicals used to break the viscosity of the fluid is referred to as a breaking agent or a breaker. In certain embodiments, the breaker is a salt or a brine solution. In other embodiments, the breaker is an encapsulated salt, where the encapsulating material is designed to degrade after a desire time of exposure to a base fluid or by the addition of an agent that disrupts the encapsulating material releasing the salt. In other embodiments, the breaker is a brine added to the fracturing fluid in an amount sufficient to break the viscosity of the fracturing fluid. The brines may be any brine solution including sodium chloride brines, calcium chloride brines, or other brines capable of reducing the viscosity of the synthetic hydratable polymers used in the fracturing fluids of this invention.

There are various methods available for breaking a fracturing fluid or a treating fluid. Typically, fluids break after the passage of time and/or prolonged exposure to high temperatures. However, it is desirable to be able to predict and control the breaking within relatively narrow limits. Mild oxidizing agents are useful as breakers when a fluid is used in a relatively high temperature formation, although formation temperatures of 300° F. (149° C.) or higher will generally break the fluid relatively quickly without the aid of an oxidizing agent.

Examples of inorganic breaking agents for use in this invention include, but are not limited to, persulfates, percarbonates, perborates, peroxides, perphosphates, permanganates, etc. Specific examples of inorganic breaking agents include, but are not limited to, alkaline earth metal persulfates, alkaline earth metal percarbonates, alkaline earth metal perborates, alkaline earth metal peroxides, alkaline earth metal perphosphates, zinc salts of peroxide, perphosphate, perborate, and percarbonate, and so on. Additional suitable breaking agents are disclosed in U.S. Pat. Nos. 5,877,127; 5,649,596; 5,669,447; 5,624,886; 5,106,518; 6,162,766; and 5,807,812, incorporated herein by reference. In some embodiments, an inorganic breaking agent is selected from alkaline earth metal or transition metal-based oxidizing agents, such as magnesium peroxides, zinc peroxides, and calcium peroxides.

In addition, enzymatic breakers may also be used in place of or in addition to a non-enzymatic breaker. Examples of suitable enzymatic breakers such as guar specific enzymes, alpha and beta amylases, amyloglucosidase, aligoglucosidase, invertase, maltase, cellulase, and hemi-cellulase are disclosed in U.S. Pat. Nos. 5,806,597 and 5,067,566, incorporated herein by reference.

A breaking agent or breaker may be used "as is" or be encapsulated and activated by a variety of mechanisms including crushing by formation closure or dissolution by formation fluids. Such techniques are disclosed, for example, in U.S. Pat. Nos. 4,506,734; 4,741,401; 5,110,486; and 3,163,219, incorporated herein by reference.

The above breaker may also be encapsulated in a polymeric coating that decomposes in the fluids at a predetermined or known rate so that the breaker are release into the system only after the encapsulation agent decomposes or the capsules break under downhole conditions.

Suitable ester compounds include any ester which is capable of assisting the breaker in degrading the viscous fluid in a controlled manner, i.e., providing delayed breaking initially and substantially complete breaking after well treatment is completed. An ester compound is defined as a compound that includes one or more carboxylate groups: R—COO—, wherein R is phenyl, methoxyphenyl, alkylphenyl, $C_1$-$C_{11}$ alkyl, $C_1$-$C_{11}$ substituted alkyl, substituted phenyl, or other organic radicals. Suitable esters include, but are not limited to, diesters, triesters, etc.

An ester is typically formed by a condensation reaction between an alcohol and an acid by eliminating one or more water molecules. Ester may hydrolyze to regenerate the organic acid, which reduces the pH of the fluid, thus decreasing a viscosity of fluid including the synthetic hydratable polymers. Other degradable polymers can be used such as PLA, PGA as delayed acid generator. Since they are solid they can also behave as fluid loss agents. Preferably, the acid is an organic acid, such as a carboxylic acid. A carboxylic acid refers to any of a family of organic acids characterized as polycarboxylic acids and by the presence of more than one carboxyl group. In additional to carbon, hydrogen, and oxygen, a carboxylic acid may include heteroatoms, such as S, N, P, B, Si, F, Cl, Br, and I. In some embodiments, a suitable ester compound is an ester of oxalic, malonic, succinic, malic, tartaric, citrate, phthalic, ethylenediaminetetraacetic (EDTA), nitrilotriacetic, phosphoric acids, etc. Moreover, suitable esters also include the esters of glycolic acid. The alkyl group in an ester that comes from the corresponding alcohol includes any alkyl group, both substituted or unsubstituted. Preferably, the alkyl group has one to about ten carbon atoms per group. It was found that the number of carbon atoms on the alkyl group affects the water solubility of the resulting ester. For example, esters made from $C_1$-$C_2$ alcohols, such as methanol and ethanol, have relatively higher water solubility. Thus, application temperature range for these esters may range from about 120° F. to about 250° F. (about 49° C. to about 121° C.). For higher temperature applications, esters formed from $C_3$-$C_{10}$ alcohols, such as n-propanol, butanol, hexanol, and cyclohexanol, may be used. Of course, esters formed from $C_{11}$ or higher alcohols may also be used. In some embodiments, mixed esters, such as acetyl methyl dibutyl citrate, may be used for high temperature applications. Mixed esters refer to those esters made from polycarboxylic acid with two or more different alcohols in a single condensation reaction. For example, acetyl methyl dibutyl citrate may be prepared by condensing citric acid with both methanol and butanol and then followed by acylation.

Specific examples of the alkyl groups originating from an alcohol include, but are not limited to, methyl, ethyl, propyl, butyl, iso-butyl, 2-butyl, t-butyl, benzyl, p-methoxybenzyl, m-methoxybenxyl, chlorobenzyl, p-chlorobenzyl, phenyl, hexyl, pentyl, etc. Specific examples of suitable ester compounds include, but are not limited to, triethyl phosphate, diethyl oxalate, dimethyl phthalate, dibutyl phthalate, diethyl maleate, diethyl tartrate, 2-ethoxyethyl acetate, ethyl acetylacetate, triethyl citrate, acetyl triethyl citrate, tetracyclohexyl EDTA, tetra-1-octyl EDTA, tetra-n-butyl EDTA, tetrabenzyl EDTA, tetramethyl EDTA, etc. Additional suitable ester compounds are described, for example, in the following U.S. Pat. Nos. 3,990,978; 3,960,736; 5,067,556; 5,224,546; 4,795,574; 5,693,837; 6,054,417; 6,069,118; 6,060,436; 6,035,936; 6,147,034; and 6,133,205, incorporated herein by reference.

When an ester of a polycarboxylic acid is used, total esterification of the acid functionality is preferred, although a partially esterified compound may also be used in place of or in addition to a totally esterified compound. In these embodiments, phosphate esters are not used alone. A phosphate ester refers to a condensation product between an alcohol and a phosphorus acid or a phosphoric acid and metal salts thereof. However, in these embodiments, combination of a polycarboxylic acid ester with a phosphate ester may be used to assist the degradation of a viscous gel.

When esters of polycarboxylic acids, such as esters of oxalic, malonic, succinic, malic, tartaric, citrate, phthalic, ethylenediaminetetraacetic (EDTA), nitrilotriacetic, and other carboxylic acids are used, it was observed that these esters assist metal based oxidizing agents (such as alkaline earth metal or zinc peroxide) in the degradation of fracturing fluids. It was found that the addition of 0.1 L/m³ to 5 L/m³ of these esters significantly improves the degradation of the fracturing fluid. More importantly, the degradation response is delayed, allowing the fracturing fluid ample time to create the fracture and place the proppant prior to the degradation reactions. The delayed reduction in viscosity is likely due to the relatively slow hydrolysis of the ester, which forms polycarboxylate anions as hydrolysis products. These polycarboxylate anions, in turn, improve the solubility of metal based oxidizing agents by sequestering the metal associated with the oxidizing agents. This may have promoted a relatively rapid decomposition of the oxidizing agent and caused the fracturing fluid degradation.

Generally, the temperature and the pH of a fracturing fluid affects the rate of hydrolysis of an ester. For downhole operations, the bottom hole static temperature ("BHST") cannot be easily controlled or changed. The pH of a fracturing fluid usually is adjusted to a level to assure proper fluid performance during the fracturing treatment. Therefore, the rate of hydrolysis of an ester could not be easily changed by altering BHST or the pH of a fracturing fluid. However, the rate of hydrolysis may be controlled by the amount of an ester used in a fracturing fluid. For higher temperature applications, the hydrolysis of an ester may be retarded or delayed by dissolving the ester in a hydrocarbon solvent. Moreover, the delay time may be adjusted by selecting esters that provide more or less water solubility. For example, for low temperature applications, polycarboxylic esters made from low molecular weight alcohols, such as methanol or ethanol, are recommended. The application temperature range for these esters could range from about 120° F. to about 250° F. (about 49° C. to about 121° C.). On the other hand, for higher temperature applications or longer injection times, esters made from higher molecular weight alcohols should preferably be used. The higher molecular weight alcohols include, but are not limited to, $C_3$-$C_6$ alcohols, e.g., n-propanol, hexanol, and cyclohexanol.

In some embodiments, esters of citric acid are used in formulating a well treatment fluid. A preferred ester of citric acid is acetyl triethyl citrate, which is available under the trade name Citraflex A2 from Morflex, Inc., Greensboro, N.C.

Gases

Suitable gases for foaming the fluid of this invention include, without limitation, nitrogen, carbon dioxide, or any other gas suitable for use in formation fracturing, or mixtures or combinations thereof.

Corrosion Inhibitors

Suitable corrosion inhibitor for use in this invention include, without limitation: quaternary ammonium salts e.g., chloride, bromides, iodides, dimethylsulfates, diethylsulfates, nitrites, bicarbonates, carbonates, hydroxides, alkoxides, or the like, or mixtures or combinations thereof; salts of nitrogen bases; or mixtures or combinations thereof. Exemplary quaternary ammonium salts include, without limitation, quaternary ammonium salts from an amine and a quaternarization agent, e.g., alkylchlorides, alkylbromide, alkyl iodides, alkyl sulfates such as dimethyl sulfate, diethyl sulfate, etc., dihalogenated alkanes such as dichloroethane, dichloropropane, dichloroethyl ether, epichlorohydrin adducts of alcohols, ethoxylates, or the like; or mixtures or combinations thereof and an amine agent, e.g., alkylpyridines, especially, highly alkylated alkylpyridines, alkyl quinolines, C6 to C24 synthetic tertiary amines, amines derived from natural products such as coconuts, or the like, dialkyl-substituted methyl amines, amines derived from the reaction of fatty acids or oils and polyamines, amidoimidazolines of DETA and fatty acids, imidazolines of ethylenediamine, imidazolines of diaminocyclohexane, imidazolines of aminoethylethylenediamine, pyrimidine of propane diamine and alkylated propene diamine, oxyalkylated mono and polyamines sufficient to convert all labile hydrogen atoms in the amines to oxygen containing groups, or the like or mixtures or combinations thereof. Exemplary examples of salts of nitrogen bases, include, without limitation, salts of nitrogen bases derived from a salt, e.g.: $C_1$ to $C_8$ monocarboxylic acids such as formic acid, acetic acid, propanoic acid, butanoic acid, pentanoic acid, hexanoic acid, heptanoic acid, octanoic acid, 2-ethylhexanoic acid, or the like; $C_2$ to $C_{12}$ dicarboxylic acids, C2 to $C_{12}$ unsaturated carboxylic acids and anhydrides, or the like; polyacids such as diglycolic acid, aspartic acid, citric acid, or the like; hydroxy acids such as lactic acid, itaconic acid, or the like; aryl and hydroxy aryl acids; naturally or synthetic amino acids; thioacids such as thioglycolic acid (TGA); free acid forms of phosphoric acid derivatives of glycol, ethoxylates, ethoxylated amine, or the like, and aminosulfonic acids; or mixtures or combinations thereof and an amine, e.g.: high molecular weight fatty acid amines such as cocoamine, tallow amines, or the like; oxyalkylated fatty acid amines; high molecular weight fatty acid polyamines (di, tri, tetra, or higher); oxyalkylated fatty acid polyamines; amino amides such as reaction products of carboxylic acid with polyamines where the equivalents of carboxylic acid is less than the equivalents of reactive amines and oxyalkylated derivatives thereof; fatty acid pyrimidines; monoimidazolines of EDA, DETA or higher ethylene amines, hexamethylene diamine (HMDA), tetramethylenediamine (TMDA), and higher analogs thereof; bisimidazolines, imidazolines of mono and polyorganic acids; oxazolines derived from monoethanol amine and fatty acids or oils, fatty acid ether amines, mono and bis amides of aminoethylpiperazine; GAA and TGA salts of the reaction products of crude tall oil or distilled tall oil with diethylene triamine; GAA and TGA salts of reaction products of dimer acids with mixtures of poly amines such as TMDA, HMDA and 1,2-diaminocyclohexane; TGA salt of imidazoline derived from DETA with tall oil fatty acids or soy bean oil, canola oil, or the like; or mixtures or combinations thereof.

Other Additives

The fracturing fluids of this invention can also include other additives as well such as scale inhibitors, carbon dioxide control additives, paraffin control additives, oxygen control additives, biocides, gel stabilizers, surfactants, clay control additives, or other additives.

Scale Control

Suitable additives for Scale Control and useful in the compositions of this invention include, without limitation: Chelating agents, e.g., $Na^+$, $K^+$ or $NH_4^+$ salts of EDTA; $Na^+$, $K^+$ or $NH_4^+$ salts of NTA; $Na^+$, $K^+$ or $NH_4^+$ salts of Erythorbic acid; $Na^+$, $K^+$ or $NH_4^+$ salts of thioglycolic acid (TGA); $Na^+$, $K^+$ or $NH_4^+$ salts of Hydroxy acetic acid; $Na^+$, $K^+$ or $NH_4^+$ salts of Citric acid; Na, K or $NH_4^+$ salts of Tartaric acid or other similar salts or mixtures or combinations thereof. Suitable additives that work on threshold effects, sequestrants, include, without limitation: Phosphates, e.g., sodium hexamethylphosphate, linear phosphate salts, salts of polyphosphoric acid, Phosphonates, e.g., nonionic such as HEDP (hydroxythylidene diphosphoric acid), PBTC (phosphoisobutane, tricarboxylic acid), Amino phosphonates of: MEA (monoethanolamine), $NH_3$, EDA (ethylene diamine), Bishydroxyethylene diamine, Bisaminoethylether, DETA (diethylenetriamine), HMDA (hexamethylene diamine), Hyper homologues and isomers of HMDA, Polyamines of EDA and DETA, Diglycolamine and homologues, or similar polyamines or mixtures or combinations thereof; Phosphate esters, e.g., polyphosphoric acid esters or phosphorus pentoxide ($P_2O_5$) esters of: alkanol amines such as MEA, DEA, triethanol amine (TEA), Bishydroxyethylethylene diamine; ethoxylated alcohols, glycerin, glycols such as EG (ethylene glycol), propylene glycol, butylene glycol, hexylene glycol, trimethylol propane, pentaeryithrol, neopentyl glycol or the like; Tris & Tetra hydroxy amines; ethoxylated alkyl phenols (limited use due to toxicity problems), Ethoxylated amines such as monoamines such as MDEA and higher amines from 2 to 24 carbons atoms, diamines 2 to 24 carbons carbon atoms, or the like; Polymers, e.g., homopolymers of aspartic acid, soluble homopolymers of acrylic acid, copolymers of acrylic acid and methacrylic acid, terpolymers of acylates, AMPS, etc., hydrolyzed polyacrylamides, poly malic anhydride (PMA); or the like; or mixtures or combinations thereof.

Carbon Dioxide Neutralization

Suitable additives for use in the fracturing fluids of this invention for $CO_2$ neutralization and for use in the compositions of this invention include, without limitation, MEA, DEA, isopropylamine, cyclohexylamine, morpholine, diamines, dimethylaminopropylamine (DMAPA), ethylene diamine, methoxy proplyamine (MOPA), dimethylethanol amine, methyldiethanolamine (MDEA) & oligomers, imidazolines of EDA and homologues and higher adducts, imidazolines of aminoethylethanolamine (AEEA), aminoethylpiperazine, aminoethylethanol amine, di-isopropanol amine, DOW AMP-90™, Angus AMP-95, dialkylamines (of methyl, ethyl, isopropyl), mono alkylamines (methyl, ethyl, isopropyl), trialkyl amines (methyl, ethyl, isopropyl), bishydroxyethylethylene diamine (THEED), or the like or mixtures or combinations thereof.

Paraffin Control

Suitable additives for use in the fracturing fluids of this invention for Paraffin Removal, Dispersion, and/or paraffin Crystal Distribution include, without limitation: Cellosolves available from DOW Chemicals Company; Cellosolve acetates; Ketones; Acetate and Formate salts and esters; surfactants composed of ethoxylated or propoxylated alcohols, alkyl phenols, and/or amines; methylesters such as coconate, laurate, soyate or other naturally occurring methylesters of fatty acids; sulfonated methylesters such as sulfonated coconate, sulfonated laurate, sulfonated soyate or other sulfonated naturally occurring methylesters of fatty acids; low molecular weight quaternary ammonium chlorides of coconut oils, soy oils or $C_{10}$ to $C_{24}$ amines or monohalogenated alkyl and aryl chlorides; quanternary ammonium salts composed of disubstituted (e.g., dicoco, etc.) and lower molecular weight halogenated alkyl and/or aryl chlorides; gemini quaternary salts of dialkyl (methyl, ethyl, propyl, mixed, etc.) tertiary amines and dihalogenated ethanes, propanes, etc. or dihalogenated ethers such as dichloroethyl ether (DCEE), or the like; gemini quaternary salts of alkyl amines or amidopropyl amines, such as cocoamidopropyldimethyl, bis quaternary ammonium salts of DCEE; or mixtures or combinations thereof. Suitable alcohols used in preparation of the surfactants include, without limitation, linear or branched alcohols, specially mixtures of alcohols reacted with ethylene oxide, propylene oxide or higher alkyleneoxide, where the resulting surfactants have a range of HLBs. Suitable alkylphenols used in preparation of the surfactants include, without limitation, nonylphenol, decylphenol, dodecylphenol or other alkylphenols where the alkyl group has between about 4 and about 30 carbon atoms. Suitable amines used in preparation of the surfactants include, without limitation, ethylene diamine (EDA), diethylenetriamine (DETA), or other polyamines. Exemplary examples include Quadrols, Tetrols, Pentrols available from BASF. Suitable alkanolamines include, without limitation, monoethanolamine (MEA), diethanolamine (DEA), reactions products of MEA and/or DEA with coconut oils and acids.

Oxygen Control

The introduction of fracturing fluids downhole often is accompanied by an increase in the oxygen content of downhole fluids due to oxygen dissolved in the introduced water. Thus, the materials introduced downhole must work in oxygen environments or must work sufficiently well until the oxygen content has been depleted by natural reactions. For a system that cannot tolerate oxygen, then oxygen must be removed or controlled in any material introduced downhole. The problem is exacerbated during the winter when the acid injected materials include winterizers such as water, alcohols, glycols, Cellosolves, formates, acetates, or the like and because oxygen solubility is higher to a range of about 14-15 ppm in very cold water. Oxygen can also increase corrosion and scaling. In CCT (capillary coiled tubing) applications using dilute solutions, the injected solutions result in injecting an oxidizing environment ($O_2$) into a reducing environment ($CO_2$, $H_2S$, organic acids, etc.).

Options for controlling oxygen content includes: (1) de-aeration of the fluid prior to downhole injection, (2) addition of normal sulfides to produce sulfur oxides, but such sulfur oxides can accelerate acid attack on metal surfaces, (3) addition of erythorbates, ascorbates, diethylhydroxyamine or other oxygen reactive compounds that are added to the fluid prior to downhole injection; and (4) addition of corrosion inhibitors or metal passivation agents such as potassium (alkali) salts of esters of glycols, polyhydric alcohol ethyloxylates or other similar corrosion inhibitors. Oxygen and corrosion inhibiting agents include mixtures of tetramethylene diamines, hexamethylene diamines, 1,2-diaminecyclohexane, amine heads, or reaction products of such amines with partial molar equivalents of aldehydes. Other oxygen control agents include salicylic and benzoic amides of polyamines, used especially in alkaline conditions, short chain acetylene diols or similar compounds, phosphate esters, borate glycerols, urea and thiourea salts of bisoxalidines or other compound that either absorb oxygen, react with oxygen or otherwise reduce or eliminate oxygen.

Salt Inhibitors

Suitable salt inhibitors for use in the fluids of this invention include, without limitation, Na Minus-Nitrilotriacetamide available from Lubrizol.

EXPERIMENTS OF THE INVENTION

TAN Salts

Examples 1-16 illustrate the formation of 4-aminomethyl-1,8-octanediamine (TAN) salts by reacting TAN with an acid component, which was either introduced directly if it was a liquid or it was dissolved in deionized water, if it was a solid. The reactions were generally carried out in a 250 ml three-neck reactor flask, with the TAN transferred to a reactor flask first and then the acid component and the reaction stirred at an elevated temperature. Table 1 tabulates certain reaction components and properties of the resulting TAN salts.

Example 1

These examples illustration the procedure used to form a TAN formate salt by reacting TAN with formic acid.

36.0 g (0.21 mol) of TAN were charged into a 250 mL three neck round bottom flask reactor equipped with a thermocouple, an Allihn water condenser, and a 100 mL additional funnel containing 30.0 g (95%, 0.63 mol) of formic acid dissolved in 15.5 g of deionized water. The reactor was cooled in an ice-water bath, and the contents of the reaction mixture were stirred using an overhead stirrer at 300 rpm. The aqueous formic acid solution was added at a rate such that the temperature did not exceed 110° F. After complete addition of formic acid, which took about 15 min, the reactor was removed from the cooling bath and refluxed at 165° F. for 30 minutes. After completion of the reaction, the contents were cooled to room temperature (75° F.). All of the other examples were carried out similarly.

TABLE 1

Reaction Data and Physical Properties of the Compounds of Examples 1-16

| Example | TAN (mol) | DI Water (mol) | Reactants | Rxn Exo (° F.) | % Solids | Properties pH | Properties SG |
|---|---|---|---|---|---|---|---|
| Example 1 | 0.21 | 0.86 | Formic acid (95%, 0.63 mol) | 165 | 58% | 7.40 | 1.13 |
| Example 2 | 0.21 | 0.86 | Formic acid (95%, 2.02 mol) | 92 | 67% | 4.80 | 1.16 |
| Example 3 | 0.21 | 0.86 | Formic acid (95%, 0.19 mol) Hydrochloric acid (36%, 0.36 mol) | 165 | 51% | 8.40 | 1.12 |
| Example 4 | 0.12 | 0.86 | Formic acid (95%, 0.09 mol); methylated TAN | NA | 22% | 4.10 | 1.13 |
| Example 5 | 0.21 | 0.86 | Acetic acid (99%, 0.62 mol) | 165 | 31% | 6.90 | 1.12 |
| Example 6 | 0.12 | 0.9 | Phosphoric acid (75%, 0.13 mol) | 165 | 48% | 10.30 | 1.20 |
| Example 7 | 0.06 | 1.8 | Fumaric acid (0.06 mol) | 178 | 57% | 10.30 | 1.13 |
| Example 8 | 0.06 | 0.9 | Fumaric acid (0.12 mol) | 151 | 44% | 3.70 | 1.14 |
| Example 9 | 0.21 | 0.86 | Hydrochloric acid ( 36%, 0.62 mol) | 165 | 50% | 7.30 | 1.10 |
| Example 10 | 0.15 | 0.9 | Methane sulfonic acid (70%, 0.35 mol) | 160 | 66% | 9.50 | 1.19 |
| Example 11 | 0.06 | 1.8 | Citric acid (0.06 mol) | 167 | 52% | 6.60 | 1.20 |
| Example 12 | 0.12 | 0.67 | Sulfuric acid (80%, 0.18 mol) | 165 | 49% | 1.20 | 1.20 |
| Example 13 | 0.12 | 0.51 | Oxalic acid (0.12 mol) | 160 | 36% | 10.50 | 1.12 |
| Example 14 | 0.06 | 1.8 | ATMP (50%, 0.03 mol) | 170 | 51% | 9.60 | 1.19 |
| Example 15 | 0.06 | 1.8 | ATMP (50%, 0.06 mol) | 180 | 52% | 4.10 | 1.21 |
| Example 16 | 0.06 | 1.8 | ATMP (50%, 0.12 mol) | 220 | 75% | 0.80 | 1.40 |
| Example 17 | 0.06 | 1.8 | Polyacrylic (0.01 mol) | 160 | 14% | 11.8 | 1.01 |
| Example 18 | 0.06 | 1.8 | ATMP (50%, 0.12 mol) | 220 | 75% | 10.9 | 1.08 |

TAN Alkylated/Quaternized Products

Examples 19-26 illustrate the formation of TAN derivatives by reacting TAN with an alkylating agent or quaternizing agent. Table 2 tabulates certain reaction data and physical properties of the resulting alkylated or quaternized TAN products.

Example 19—TAN Methylation

Step 1: Methylation 94.4 g, 95%, 3.2 mol of paraformaldehyde and 145.6 g, 95%, 3.0 mol of formic acid were combined in a 0.5 L resin kettle equipped with a thermocouple, Allihn water condenser, and a 100 mL dropping funnel containing 83.8 g. 0.48 mol of TAN. The contents of the flask were stirred using an overhead stirrer. The TAN was added over 280 minutes, keeping the mixture under 104° F. When addition was completed, the mixture was stirred for another 20 minutes and then refluxed at 165° F. for 3.0-5.5 hour. The final product was a light brown liquid. Solids=28.1%, pH=7.7, d=1.10 g/mL.

Example 20—TAN Benzyl Quaternization

Step 1: Methylation 70.8 g, 95%, 2.4 mol of paraformaldehyde and 109.2 g, 95%, 2.4 mol formic acid were combined in a 0.5 L resin kettle equipped with a thermocouple, Allihn water condenser, and a 100 mL dropping funnel containing 62.9 g, 95%, 0.36 mol of TAN. The contents of the flask were stirred using an overhead stirrer. The TAN was added over 150 minutes, keeping the mixture under 117° F.

Step 2: Quaternization with Benzyl Chloride

Half of the above mixture was mixed with 2.0 mL isopropyl alcohol and refluxed at 181° F.-189° F. for 220 min, during which time the product turned a slight red color. 33.0 g, 99%, 0.26 mol of benzyl chloride were added, followed by refluxing for 150 min at 194° F. The resulting product was soluble in water. Solids=49.6%, pH=3.1, d=1.14 g/mL.

Example 21—TAN (±) Epichlorohydrin Quaternization

Step 1: Methylation 70.8 g, 95%, 2.4 mol of paraformaldehyde and 109.2 g, 95%, 2.4 mol of formic acid were combined in a 0.5 L resin kettle equipped with a thermocouple, Allihn water condenser, and a 100 mL dopping funnel containing 62.9 g, 95%, 0.36 mol TAN. The contents of the flask were stirred using an overhead stirrer. The TAN was added over 150 minutes, keeping the mixture under 117° F.

Step 2: Quaternization with Epichlorohydrin

Half of the above mixture was mixed with 2.0 mL isopropyl alcohol and refluxed at 181° F.-189° F. for 220 min, during which time the product turned a slight red color. 50 g, 98%, 0.54 mol of (±)epichlorohydrin were added, followed by refluxing at 140° F.-194° F. for 7 hours. The resulting product was soluble in water. Solids=53.0%, pH=3.8, d=1.21 g/mL.

Example 22—TAN bis(2-Chloroethyl)ether Quaternization

Step 2: Quaternization with bis(2-chloroethyl)ether

The other half of above mixture was mixed with 28.3 g, 99%, 0.20 mol of bis(2-chloroethyl) ether) and refluxed at 212° F. for 13.5 h. The final product was a light orange red color. Solids=46.4%, pH=3.2, d=1.13 g/mL.

Example 23—TAN Diethyl Sulfate Quaternization 1

Step 1: Methylation 70.8 g, 95%, 2.4 mol of paraformaldehyde and 109.2 g, 95%, 2.4 mol of formic acid were combined in a 0.5 L resin kettle equipped with a thermocouple, Allihn water condenser, and a 100 mL dropping funnel containing 62.9 g, 95%, 0.36 mol TAN. The contents of the flask were stirred using an overhead stirrer. The TAN was added over 150 minutes, keeping the mixture under 117° F.

Step 2: Quaternization with Diethyl Sulfate

Half of the above mixture was mixed with 2.0 mL isopropyl alcohol and refluxed at 83° F.-87° C. for 220 min, during which time the product turned a slight red color. 41.6 g, 98%, 0.26 mol of diethyl sulfate were added, followed by refluxing for 150 min at 140° F.-194° F. The resulting product was soluble in water. Solids=63.7%, pH=5.0, d=1.17 g/mL.

Example 24—TAN Diethyl Sulfate Quaternization 2

Step 2: Quaternization with Diethyl Sulfate

The other half of above mixture was mixed with 2.0 mL isopropyl alcohol and 20 mL DI water, and refluxed at 90° C. for 180 min, during which time the product turned a slight red color. 83.3 g, 98%, 0.53 mol of diethyl sulfate were added, followed by refluxing for 240 min at 176° F. The resulting product was soluble in water. Solids=52.4%, pH=0.8, d=1.15 g/mL.

Example 25—TAN Diethyl Sulfate Quaternization 3

Step 1: Methylation 70.8 g, 95%, 2.4 mol of paraformaldehyde and 109.2 g, 95%, 2.4 mol of formic acid were combined in a 0.5 L resin kettle equipped with a thermocouple, Allihn water condenser, and a 100 mL dropping funnel containing 62.9 g, 95%, 0.36 mol TAN. The contents of the flask were stirred using an overhead stirrer at 300 rpm. The TAN was added over 120 minutes, keeping the mixture under 131° F. 25 mL of Deionized water and 5 mL isopropanol were added to the flask, and heating was continued at 185° F. for another 180 minutes. The final product is a light brown liquid. Solids=19.6%, pH=6.4, d=1.08 g/mL.

Step 2: Quaternization with Diethyl Sulfate 100.0 g of the above liquid were charged into a 0.5 L resin kettle equipped with a thermocouple, Allihn water condenser, and a 100 mL dropping funnel containing 11.8 g, 98%, 0.08 mol of diethyl sulfate (DES). The contents of the flask were stirred using an overhead stirrer at 300 rpm. The DES was added over 30 minutes, and then refluxed at 145° F. for 90 minutes. The final product is a light red-brown liquid. Solids=28.6%, pH=5.2, d=1.1 g/mL.

Example 26—TAN Epichlorohydrin Alkylation 30.0 g, 0.18 mol TAN, 20.0 g, 1.1 mol deionized water were charged into a 250 mL three neck round bottom flask reactor equipped with a thermocouple, Allihn water condenser, and a 100 mL additional funnel with 16.2 g, 0.18 mol (±) epichlorohydrin. The reactor was cooled in an ice-water bath, and the contents of the reaction mixture were stirred using an overhead stirrer at 300 rpm. The aqueous (±) epichlorohydrin solution was added at a rate such that the temperature did not exceed 110° F. After complete addition over a 15 min period of time of the (±) epichlorohydrin, the reactor was removed from the cooling bath and refluxed at 144° F. for 2.5 h. The reactor was then cooled to 75° F. The process was repeated with the addition of a $2^{nd}$ portion of 16.2 g of (±) epichlorohydrin, followed by continued heating at 158° F. for 2.0 h. The process was repeated with a $3^{rd}$ portion of 16.2 g (±) epichlorohydrin and refluxed under the same conditions as above. After completion of the reaction, the contents were cooled to room temperature. Solids=55%, pH=5.7, d=1.2 g/mL.

TABLE 2

Reaction Data and Physical Properties of Compounds of Examples 19-26

| Example | TAN (mol) | DI Water (mol) | Reactants | Rxn Exo (° F.) | % Solids | Properties pH | SG |
|---|---|---|---|---|---|---|---|
| Example 19 | 0.48 | NA | Paraformaldehyde (95%, 3.2 mol) Formic acid (95%, 3.0 mol) | NA | 28% | 7.70 | 1.10 |
| Example 20 | 0.18 | NA | Benzyl chloride (99%, 0.26 mol) | NA | 50% | 3.10 | 1.14 |
| Example 21 | 0.18 | NA | (±) Epichlorohydrin (98%, 0.54 mol) | NA | 53% | 3.80 | 1.21 |
| Example 22 | 0.18 | NA | bis(2-chloroethyl) ether (99%, 0.20 mol) | NA | 46% | 3.20 | 1.13 |
| Example 23 | 0.18 | NA | Diethyl sulfate (98%, 0.26 mol) | NA | 64% | 5.00 | 1.17 |
| Example 24 | 0.18 | NA | Diethyl sulfate (98%, 0.53 mol) | NA | 52% | 0.80 | 1.15 |
| Example 25 | 0.15 | NA | Diethyl sulfate (98%, 0.08 mol) | NA | 29% | 6.40 | 1.08 |
| Example 26 | 0.18 | NA | (±) Epichlorohydrin (98%, 0.54 mol) | NA | 55% | 5.70 | 1.20 |

Capillary Suction Time (CST) Tests at 73° F.

Measure 500 mL of DI water into a 1 L waring blender jar and add 1.0 gpt (0.5 mL) of clay stabilizer. Stir to dissolve, then add 5.0 g of non-treated sodium bentonite, 13A API section 10. With a Variac variable transformer set at approximately 30%, blend for 2 minutes. Immediately measure 5.0 mL of slurry and inject into the sample holder of the Ofite capillary suction timer (part no. 294-50), which is placed on a Whatman filter paper (part no. 3017-820). The timer starts when the liquid reaches the first concentric electrode, and stops when it reaches the second concentric electrode. CST times for Examples 1-26 and comparison products Comp 1-14 are found in Table 3.

TABLE 3

CST Times at 1 gpt for Example 1-26 and Comparative Examples 1-14 at 1 gpt

| Example | Product Description | Activity | Tested gpt | CST time |
|---|---|---|---|---|
| Example 1 | TAN Formate | 58% | 1 | 14.3 |
| Example 2 | TAN Formate | 67% | 1 | 14.3 |
| Example 3 | TAN Formate/Hydrochloride | 51% | 1 | 20.1 |
| Example 4 | Methylated TAN Formate | 22% | 1 | 16.6 |
| Example 5 | TAN Acetate | 31% | 1 | 14.9 |
| Example 6 | TAN Phosphate | 48% | 1 | 23.5 |
| Example 7 | TAN Fumarate | 57% | 1 | 23.9 |
| Example 8 | TAN Fumarate | 44% | 1 | 97.4 |
| Example 9 | TAN Hydrochloride | 50% | 1 | 43.3 |
| Example 10 | TAN Methane Sulfonate | 66% | 1 | 53.7 |
| Example 11 | TAN Citrate | 52% | 1 | 61.3 |
| Example 12 | TAN Sulfate | 49% | 1 | 61.4 |
| Example 13 | TAN Oxalate | 36% | 1 | 97.2 |
| Example 14 | TAN-ATMP | 51% | 1 | 133 |
| Example 15 | TAN-ATMP | 52% | 1 | 192.1 |

TABLE 3-continued

CST Times at 1 gpt for Example 1-26 and Comparative Examples 1-14 at 1 gpt

| Example | Product Description | Activity | Tested gpt | CST time |
|---|---|---|---|---|
| Example 16 | TAN-ATMP | 75% | 1 | 171.4 |
| Example 17 | TAN Polyacrylate | 14% | 1 | 152.1 |
| Example 18 | TAN p-Toluene Sulfonate | 44% | 1 | 173.3 |
| Example 19 | TAN Methylation | 28% | 1 | 21.60 |
| Example 20 | TAN Benzyl Quat | 50% | 1 | 13.9 |
| Example 21 | TAN (±) Epichlorohydrine Quat | 53% | 1 | 24.30 |
| Example 22 | TAN Chloroethylether Quat | 46% | 1 | 27.60 |
| Example 23 | TAN Diethyl Sulfate Quat 1 | 64% | 1 | 31.00 |
| Example 24 | TAN Diethyl Sulfate Quat 2 | 52% | 1 | 40.90 |
| Example 25 | TAN Diethyl Sulfate Quat 3 | 29% | 1 | 113.80 |
| Example 26 | TAN (±) Epichlorohydrin | 55% | 1 | 43.70 |
| Comp 1 | Potassium Formate | 2% | 1 | 16.80 |
| Comp 2 | Potassium Chloride | 2% | 1 | 23.50 |
| Comp 3 | Potassium Acetate | 2% | 1 | 41.10 |
| Comp 4 | Choline Chloride | 68% | 1 | 175.30 |
| Comp 5 | Diethylenetriamine Benzyl Quat | 40% | 1 | 206.20 |
| Comp 6 | Hexamethylenediamine salt | 42% | 1 | 134.50 |
| Comp 7 | Polyamine mixture | 52% | 1 | 208.10 |
| Comp 8 | Polyamine Quat | 23% | 1 | 265.50 |
| Comp 9 | Polyamine Quat | 43% | 1 | 51.40 |
| Comp 10 | Alkyl Polyglucoside | 17% | 1 | 449.40 |
| Comp 11 | Alkyl Polyglucoside | 35% | 1 | 612.20 |
| Comp 12 | Polyglucoside Glycinate | 37% | 1 | 553.80 |
| Comp 13 | Alkyl Polyglucoside Quat | 28% | 1 | 591.50 |
| Comp 14 | Alkyl Polyglucoside | 39% | 1 | 652.20 |

Coreflood Experiments 2 wt % KCl brine and DI water were used in the coreflood experiments. The density and viscosity of the brine were 1.008 g/cm³ and 0.98 cP, respectively, at 68° F. The coreflood experimental condition was 200° F., and there was a backpressure of 500 psi at the outlet. Bandera sandstone cores were used in the coreflood experiments. The mineralogy of Bandera sandstone was determined by X-ray diffraction.

Experimental Steps

The coreflood experiments were carried out using the following steps:
1. Cores were dried in the oven at 250° F. for at least 5 hours. The weight of the dry cores is measured.
2. The cores were saturated with 2 wt. % KCl brine under vacuum for 4 hours and then weighed again. The pore volume was calculated from the difference in weights.
3. Initial permeability was measured using brine when the differential pressure stabilizes at different flow rates.
4. Brine was injected into the core until the pressure drop stabilizes at 200° F.
5. Two PV of the clay stabilizer treatment was injected through the core, followed by DI water.
6. The permeability of each core was compared before and after clay stabilizer treatment.

The improvement factor is expressed as a ratio of effective gas permeability after the clay stabilizer treatment to the effective gas permeability before the clay stabilizer treatment and is given by the formula:

$$\text{Improvement Factor} = \frac{K_f}{K_i}$$

where $K_f$ is the final core gas permeability after treatment and $K_i$ is the initial (untreated) core gas permeability.

All references cited herein are incorporated by reference. Although the disclosure has been disclosed with reference to its preferred embodiments, from reading this description those of skill in the art may appreciate changes and modification that may be made which do not depart from the scope and spirit of the disclosure as described above and claimed hereafter.

We claim:

1. A method comprising:
injecting, into a subterranean formation under fracturing conditions, one or more fracturing fluid compositions comprising:
a base fluid;
(a) one or more synthetic or natural hydratable polymers; (b) one or more synthetic or natural hydratable polymers and one or more crosslinking agents; or (c) one or more synthetic or natural hydratable polymers, one or more crosslinking agents, and one or more proppants; and
an effective amount of a clay stabilizing composition comprising:
one or more tri-functional primary amine compounds comprising one or more compounds of Formula I:

$$HC(RNR^1R^2)(R'NR^3R^4)(R''NR^5R^6) \qquad (I); \text{ and}$$

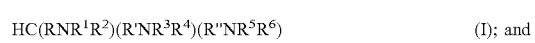

one or more salts comprising one or more compounds of Formula II:

$$HC(RN^+R^1R^2R^7)(R'N^+R^3R^4R^8)(R''N^+R^5R^6R^9)X_n \qquad (II),$$

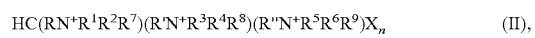

wherein:
the R, R', and R'' groups comprising the same or different hydrocarbyl linking groups including between 1 and 8 carbon atoms, and when the R, R', and R'' groups including between 2 and 8 carbon atoms, then one or more carbon atoms may be replaced by acetate groups, or carbonyl groups, the $R^{1-6}$ groups comprising the same or different hydrogen atoms or hydrocarbyl groups including between 1 and 6 carbon atoms, and when the $R^{1-6}$ groups including between 2 and 6 carbon atoms, then one or more carbon atoms may be replaced by oxygen atoms, acetate groups, or carbonyl groups, the $R^{7-9}$ groups are (a) absent and their associated nitrogen atoms do not bear a charge, (b) the same or different comprising a hydrogen atom and their associated nitrogen atoms bear a charge, or (c) the same or different comprising a hydrocarbyl group including between 1 and 24 carbon atoms and their associated nitrogen atoms bear a charge; provided that at least one of the $R^{7-9}$ groups comprising a hydrogen atom or a hydrocarbyl group, and when the $R^{7-9}$ groups including between 2 and 24 carbon atoms, then one or more carbon atoms may be replaced by oxygen atoms, acetate groups, or carbonyl groups;

the X groups are the same or different counterions derived from an organic acid, an alkylating agent, a quaternizing agent, or mixtures thereof;

n is an integer having a value of 1, 2 or 3; provided that each of the compounds of Formula (II) is neutral;

the clay stabilizing composition stabilizes clay, reduces clay swelling, and reduces fines migration during fracturing.

2. The method of claim 1, wherein, in the fracturing step:

the R, R', and R" groups comprising the same or different linear alkyl linking groups of the formula —$(CH_2)_m$—;

m is an integer having a value between 1 and 8, when m has a value between 2 and 8, then one or more carbon atoms may be replaced by oxygen atoms;

the R group comprising a linear alkyl linking group having between 1 and 3 carbon atoms;

the R' group comprising linear alkyl linking group having between 2 and 4 carbon atoms;

the R" group comprising linear alkyl linking groups having between 3 and 5 carbon atoms.

3. The method of claim 1, wherein, in the fracturing step:

the one or more compounds of Formula (I) comprising 3-aminomethyl-1,6-hexanediamine, 3-aminoethyl-1,6-hexanediamine, 3-aminomethyl-1,7-heptanediamine, 3-aminoethyl-1,7-heptanediamine, 3-aminopropyl-1,7-hexanediamine, 4-aminomethyl-1,8-octanediamine (triaminononane (TAN)), 4-aminoethyl-1,8-octanediamine, 4-aminopropyl-1,8-octanediamine, 4-aminomethyl-1,9-noanediamine, 4-aminoethyl-1,9-nonanediamine, 4-aminopropyl-1,9-nonanediamine, 4-aminomethyl-1,10-decanediamine, 4-aminoethyl-1,10-decanediamine, 4-aminopropyl-1,10-decanediamine, 4-aminobutyl-1,10-decanediamine, 3-dimethylaminomethyl-1,6-hexanedimethylamine, 3-dimethylaminoethyl-1,6-hexanedimethylamine, 3-dimethylaminomethyl-1,7-heptanedimethylamine, 3-dimethylaminoethyl-1,7-heptanedimethylamine, 3-dimethylaminopropyl-1,7-hexanedimethylamine, 4-dimethylaminomethyl-1,8-octanedimethylamine, 4-dimethylaminoethyl-1,8-octanedimethylamine, 4-dimethylaminopropyl-1,8-octanedimethylamine, 4-dimethylaminomethyl-1,9-noanedimethylamine, 4-dimethylaminoethyl-1,9-nonanedimethylamine, 4-dimethylaminopropyl-1,9-nonanedimethylamine, 4-dimethylaminomethyl-1,10-decanedimethylamine, 4-dimethylaminoethyl-1,10-decanedimethylamine, 4-dimethylaminopropyl-1,10-decanedimethylamine, 4-dimethylaminobutyl-1,10-decanedimethylamine, 3-diethylaminomethyl-1,6-hexanediethylamine, 3-diethylaminoethyl-1,6-hexanediethylamine, 3-diethylaminomethyl-1,7-heptanediethylamine, 3-diethylaminoethyl-1,7-heptanediethylamine, 3-diethylaminopropyl-1,7-hexanediethylamine, 4-diethylaminomethyl-1,8-octanediethylamine, 4-diethylaminoethyl-1,8-octanediethylamine, 4-diethylaminopropyl-1,8-octanediethylamine, 4-diethylaminomethyl-1,9-noanediethylamine, 4-diethylaminoethyl-1,9-nonanediethylamine, 4-diethylaminopropyl-1,9-nonanediethylamine, 4-diethylaminomethyl-1,10-decanediethylamine, 4-diethylaminoethyl-1,10-decanediethylamine, 4-diethylaminopropyl-1,10-decanediethylamine, 4-diethylaminobutyl-1,10-decanediethylamine, 3-methylethylaminomethyl-1,6-hexanemethylethylamine, 3-methylethylaminoethyl-1,6-hexanemethylethylamine, 3-methylethylaminomethyl-1,7-heptanemethylethylamine, 3-methylethylaminoethyl-1,7-heptanemethylethylamine, 3-methylethylaminopropyl-1,7-hexanemethylethylamine, 4-methylethylaminomethyl-1,8-octanemethylethylamine, 4-methylethylaminoethyl-1,8-octanemethylethylamine, 4-methylethylaminopropyl-1,8-octanemethylethylamine, 4-methylethylaminomethyl-1,9-noanemethylethylamine, 4-methylethylaminoethyl-1,9-nonanemethylethylamine, 4-methylethylaminopropyl-1,9-nonanemethylethylamine, 4-methylethylaminomethyl-1,10-decanemethylethylamine, 4-methylethylaminoethyl-1,10-decanemethylethylamine, 4-methylethylaminopropyl-1,10-decanemethylethylamine, 4-methylethylaminobutyl-1,10-decanemethylethylamine, quaternized derivatives thereof, or mixtures thereof;

the organic acids comprising formic acid, acetic acid, citric acid, lactic acid, fumaric acid, aminotris(methylenephosphonic acid) (ATMP), polyacrylic acid, p-toluene sulfonic acid, or mixtures thereof;

the alkylating agents comprising: (a) dialkylsulfates, wherein the alkyl groups are the same or different and have between 1 and 6 carbon atoms; (b) chloroalkylbenzenes, wherein the alkyl group has between 1 and 6 carbon atoms; (c) alkylchlorides, wherein the alkyl group has between 1 and 24 carbon atoms; (d) chloroethers having between 4 and 24 carbon atoms; (e) alkylsulfonates, wherein the alkyl group comprising a straight chain alkyl group, a branched alkyl group, or a cyclic alkyl group having between 1 to 24 carbon atoms; or (f) mixtures thereof;

the quaternizing agents comprising: (a) dialkylsulfates, wherein the alkyl groups are the same or different and have between 1 and 6 carbon atoms; (b) chloroalkylbenzenes, wherein the alkyl group has between 1 and 6 carbon atoms; (c) alkylchlorides, wherein the alkyl group has between 1 and 24 carbon atoms; (d) chloroethers having between 4 and 24 carbon atoms; (e) alkylsulfonates, wherein the alkyl group comprising a straight chain alkyl group, or branched alkyl group, or cyclic alkyl group has between 1 to 24 carbon atoms; or (f) mixtures thereof.

4. The method of claim 3, wherein, in the fracturing step:

the dialkylsulfate compounds comprising dimethylsulfate, methylethylsulfate, diethylsulfate, dipropylsulfate, methylpropylsulfate, ethylpropylsulfate, and mixed dialkyl sulfates, or mixtures thereof;

the chloroalkylbenzenes comprising benzyl chloride, chloroxylene, chloroethylbenzene, chloropropylbenzene, chlorobutylbenzene, or mixtures thereof;

alkylchlorides include methyl chloride, ethyl chloride, propyl chloride, butyl chloride, pentyl chloride, hexyl chloride, heptyl chloride, octyl chloride, 1-chlorohexadecane, or mixtures thereof;

chloroethers comprising chloroethylethanolether, dichloroethylether, or mixtures thereof;

alkylsulfonates comprising methylsulfonate, ethane sulfonic acid, 1-butane sulfonic acid, petroleum sulfonic acids, benzenesulfonic acid, toluene sulfonic acid, dedecylbenzene sulfonic acid, or mixtures thereof.

5. The method of claim 1, wherein, in the fracturing step;
the one or more compounds of Formula (I) comprising:
one or more compounds of Formula (III):

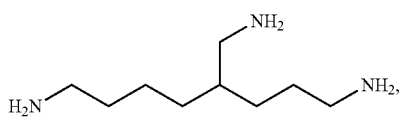

(III)

one or more compounds of Formula (V):

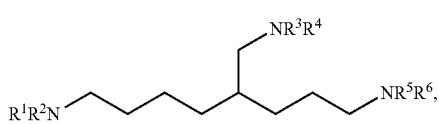

(V)

or
mixtures thereof;
the one or more compounds of Formula (II) comprising:
one or more compounds of Formula (IV):

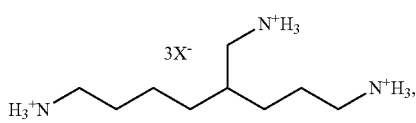

(IV)

one or more compounds of Formula (VI):

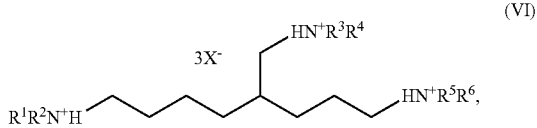

(VI)

one or more compounds of Formula (VII):

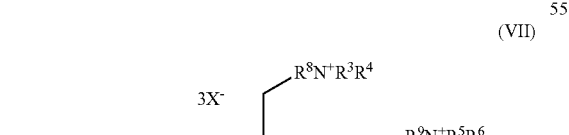

(VII)

or
mixtures thereof.

6. The method of claim 5, wherein, in the fracturing step: the one compound of Formula (I) comprising 4-aminomethyl-1,8-octanediamine (TAN);
the one or more salts of Formula (II) comprising:
  TAN formate salts,
  methylated TAN formate salts,
  TAN acetate salts,
  TAN fumarate salts,
  TAN citrate salts,
  TAN oxalate salts,
  TAN p-toluene sulfonate salts,
  TAN methane sulfonate salts,
  TAN aminotris(methylenephosphonic acid) salts,
  TAN polyacrylate salts,
  methylated TAN salts,
  TAN benzyl quaternary salts,
  TAN (±) epichlorohydrine quaternary salts,
  TAN chloroethylether quaternary salts,
  TAN diethyl sulfate quaternary salts,
  TAN (±) epichlorohydrin salts, or
  mixtures thereof;
the base fluid comprising:
  aqueous base fluids comprising freshwater, production water, seawater, non-sodium brines, aqueous makeup systems, or mixture thereof; and
  oil based fluids comprising synthetic hydrocarbon fluids, petroleum based hydrocarbon fluids, natural hydrocarbon fluids, or mixtures thereof.

7. The method of claim 6, wherein, in the fracturing step:
the one or more salts of Formula (III) comprising:
  TAN formate salts,
  TAN fumarate salts,
  TAN citrate salts,
  TAN p-toluene sulfonate salts,
  TAN methane sulfonate salts,
  TAN aminotris(methylenephosphonic acid) salts,
  TAN benzyl quaternary salts,
  TAN (±) epichlorohydrine quaternary salts,
  TAN chloroethylether quaternary salts,
  TAN diethyl sulfate quaternary salts,
  TAN (±) epichlorohydrin salts, or
  mixtures thereof.

8. The method of claim 7, wherein, in the fracturing step:
the one or more salts of Formula (IV) comprising:
  TAN formate salts,
  TAN fumarate salts,
  TAN citrate salts,
  TAN p-toluene sulfonate salts,
  TAN methane sulfonate salts,
  TAN aminotris(methylenephosphonic acid) salts,
  TAN benzyl quaternary salts,
  TAN (±) epichlorohydrine quaternary salts,
  TAN chloroethylether quaternary salts,
  TAN diethyl sulfate quaternary salts,
  TAN (±) epichlorohydrin salts, or
  mixtures thereof.

9. The method of claim 8, wherein, in the fracturing step:
the one or more salts of Formula (V) comprising:
  TAN formate salts,
  TAN methane sulfonate salts,
  TAN aminotris(methylenephosphonic acid) salts,
  TAN diethyl sulfate quaternary salts, or
  mixtures thereof.

10. A method comprising:
injecting, into a subterranean formation under fracturing conditions, one or more first fracturing fluid compositions comprising:
  a first base fluid;
  one or more first synthetic and/or natural hydratable polymers;

one or more first crosslinking agents; and
an effective amount of a clay stabilizing composition;
injecting, into a subterranean formation under fracturing conditions, one or more second fracturing fluid compositions comprising:
a second base fluid;
one or more second synthetic and/or natural hydratable polymers;
one or more second crosslinking agents;
one or more proppants; and
an effective amount of the clay stabilizing composition,
wherein:
the clay stabilizing composition comprising:
one or more tri-functional primary amine compounds comprising one or more compounds of Formula I:

$$HC(RNR^1R^2)(R'NR^3R^4)(R''NR^5R^6) \quad (I); \text{ and}$$

one or more salts comprising one or more compounds of Formula II:

$$HC(RN^+R^1R^2R^7)(R'N^+R^3R^4R^8)(R''N^+R^5R^6R^9)X_n \quad (II),$$

the R, R', and R'' groups comprising the same or different hydrocarbyl linking groups including between 1 and 8 carbon atoms, and when the R, R', and R'' groups including between 2 and 8 carbon atoms, then one or more carbon atoms may be replaced by acetate groups, or carbonyl groups,
the $R^{1-6}$ groups comprising the same or different hydrogen atoms or hydrocarbyl groups including between 1 and 6 carbon atoms, and when the $R^{1-6}$ groups including between 2 and 6 carbon atoms, then one or more carbon atoms may be replaced by oxygen atoms, acetate groups, or carbonyl groups,
the $R^{7-9}$ groups are (a) absent and their associated nitrogen atoms do not bear a charge, (b) the same or different comprising a hydrogen atom and their associated nitrogen atoms bear a charge, or (c) the same or different comprising a hydrocarbyl group including between 1 and 24 carbon atoms and their associated nitrogen atoms bear a charge; provided that at least one of the $R^{7-9}$ groups comprising a hydrogen atom or a hydrocarbyl group, and when the $R^{7-9}$ groups including between 2 and 24 carbon atoms, then one or more carbon atoms may be replaced by oxygen atoms, acetate groups, or carbonyl groups;
the X groups are the same or different counterions derived from an organic acid, an alkylating agent, a quaternizing agent, or mixtures thereof;
n is an integer having a value of 1, 2 or 3; provided that each of the compounds of Formula (II) is neutral;
the clay stabilizing composition stabilizes clay, reduces clay swelling, and reduces fines migration during fracturing.

11. The method of claim 10, wherein, in the fracturing step:
the R, R', and R'' groups comprising the same or different linear alkyl linking groups of the formula —$(CH_2)_m$—;
m is an integer having a value between 1 and 8, when m has a value between 2 and 8, then one or more carbon atoms may be replaced by oxygen atoms;
the R group comprising a linear alkyl linking group having between 1 and 3 carbon atoms;
the R' group comprising linear alkyl linking group having between 2 and 4 carbon atoms;
the R'' group comprising linear alkyl linking groups having between 3 and 5 carbon atoms.

12. The method of claim 10, wherein, in the fracturing step:
the one or more compounds of Formula (I) comprising 3-aminomethyl-1,6-hexanediamine, 3-aminoethyl-1,6-hexanediamine, 3-aminomethyl-1,7-heptanediamine, 3-aminoethyl-1,7-heptanediamine, 3-aminopropyl-1,7-hexanediamine, 4-aminomethyl-1,8-octanediamine (triaminononane (TAN)), 4-aminoethyl-1,8-octanediamine, 4-aminopropyl-1,8-octanediamine, 4-aminomethyl-1,9-noanediamine, 4-aminoethyl-1,9-nonanediamine, 4-aminopropyl-1,9-nonanediamine, 4-aminomethyl-1,10-decanediamine, 4-aminoethyl-1,10-decanediamine, 4-aminopropyl-1,10-decanediamine, 4-aminobutyl-1,10-decanediamine, 3-dimethylaminomethyl-1,6-hexanedimethylamine, 3-dimethylaminoethyl-1,6-hexanedimethylamine, 3-dimethylaminomethyl-1,7-heptanedimethylamine, 3-dimethylaminoethyl-1,7-heptanedimethylamine, 3-dimethylaminopropyl-1,7-hexanedimethylamine, 4-dimethylaminomethyl-1,8-octanedimethylamine, 4-dimethylaminoethyl-1,8-octanedimethylamine, 4-dimethylaminopropyl-1,8-octanedimethylamine, 4-dimethylaminomethyl-1,9-noanedimethylamine, 4-dimethylaminoethyl-1,9-nonanedimethylamine, 4-dimethylaminopropyl-1,9-nonanedimethylamine, 4-dimethylaminomethyl-1,10-decanedimethylamine, 4-dimethylaminoethyl-1,10-decanedimethylamine, 4-dimethylaminopropyl-1,10-decanedimethylamine, 4-dimethylaminobutyl-1,10-decanedimethylamine, 3-diethylaminomethyl-1,6-hexanediethylamine, 3-diethylaminoethyl-1,6-hexanediethylamine, 3-diethylaminomethyl-1,7-heptanediethylamine, 3-diethylaminoethyl-1,7-heptanediethylamine, 3-diethylaminopropyl-1,7-hexanediethylamine, 4-diethylaminomethyl-1,8-octanediethylamine, 4-diethylaminoethyl-1,8-octanediethylamine, 4-diethylaminopropyl-1,8-octanediethylamine, 4-diethylaminomethyl-1,9-noanediethylamine, 4-diethylaminoethyl-1,9-nonanediethylamine, 4-diethylaminopropyl-1,9-nonanediethylamine, 4-diethylaminomethyl-1,10-decanediethylamine, 4-diethylaminoethyl-1,10-decanediethylamine, 4-diethylaminopropyl-1,10-decanediethylamine, 4-diethylaminobutyl-1,10-decanediethylamine, 3-methylethylaminomethyl-1,6-hexanemethylethylamine, 3-methylethylaminoethyl-1,6-hexanemethylethylamine, 3-methylethylaminomethyl-1,7-heptanemethylethylamine, 3-methylethylaminoethyl-1,7-heptanemethylethylamine, 3-methylethylaminopropyl-1,7-hexanemethylethylamine, 4-methylethylaminomethyl-1,8-octanemethylethylamine, 4-methylethylaminoethyl-1,8-octanemethylethylamine, 4-methylethylaminopropyl-1,8-octanemethylethylamine, 4-methylethylaminomethyl-1,9-noanemethylethylamine, 4-methylethylaminoethyl-1,9-nonanemethylethylamine, 4-methylethylaminopropyl-1,9-nonanemethylethylamine, 4-methylethylaminomethyl-1,10-decanemethylethylamine, 4-methylethylaminoethyl-1,10-decanemethylethylamine, 4-methylethylaminopropyl-1,10-decanemethylethylamine, 4-methylethylaminobutyl-1,10-decanemethylethylamine, quaternized derivatives thereof, or mixtures thereof;
the organic acids comprising formic acid, acetic acid, citric acid, lactic acid, fumaric acid, aminotris(methylenephosphonic acid) (ATMP), polyacrylic acid, p-toluene sulfonic acid, or mixtures thereof;

the alkylating agents comprising: (a) dialkylsulfates, wherein the alkyl groups are the same or different and have between 1 and 6 carbon atoms; (b) chloroalkylbenzenes, wherein the alkyl group has between 1 and 6 carbon atoms; (c) alkylchlorides, wherein the alkyl group has between 1 and 24 carbon atoms; (d) chloroethers having between 4 and 24 carbon atoms; (e) alkylsulfonates, wherein the alkyl group comprising a straight chain alkyl group, a branched alkyl group, or a cyclic alkyl group having between 1 to 24 carbon atoms; or (f) mixtures thereof;

the quaternizing agents comprising: (a) dialkylsulfates, wherein the alkyl groups are the same or different and have between 1 and 6 carbon atoms; (b) chloroalkylbenzenes, wherein the alkyl group has between 1 and 6 carbon atoms; (c) alkylchlorides, wherein the alkyl group has between 1 and 24 carbon atoms; (d) chloroethers having between 4 and 24 carbon atoms; (e) alkylsulfonates, wherein the alkyl group comprising a straight chain alkyl group, or branched alkyl group, or cyclic alkyl group has between 1 to 24 carbon atoms; or (f) mixtures thereof.

13. The method of claim 12, wherein, in the fracturing step:

the dialkylsulfate compounds comprising dimethylsulfate, methylethylsulfate, diethylsulfate, dipropylsulfate, methylpropylsulfate, ethylpropylsulfate, higher dialkyl sulfates and mixed dialkyl sulfates, or mixtures thereof;

the chloroalkylbenzenes comprising benzyl chloride, chloroxylene, chloroethylbenzene, chloropropylbenzene, chlorobutylbenzene, or mixtures thereof;

alkylchlorides include methyl chloride, ethyl chloride, propyl chloride, butyl chloride, pentyl chloride, hexyl chloride, heptyl chloride, octyl chloride, 1-chlorohexadecane, or mixtures thereof;

chloroethers comprising chloroethylethanolether, dichloroethylether, or mixtures thereof;

alkylsulfonates comprising methylsulfonate, ethane sulfonic acid, 1-butane sulfonic acid, petroleum sulfonic acids, benzenesulfonic acid, toluene sulfonic acid, dedecylbenzene sulfonic acid, or mixtures thereof.

14. The method of claim 13, wherein, in the fracturing step;

the one or more compounds of Formula (I) comprising:
one or more compounds of Formula (III):

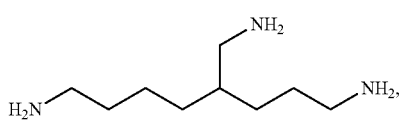
(III)

one or more compounds of Formula (V):

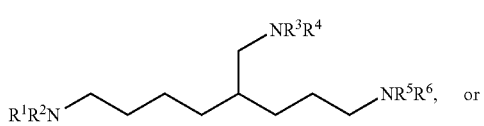
(V)

or mixtures thereof;

the one or more compounds of Formula (II) comprising:
one or more compounds of Formula (IV):

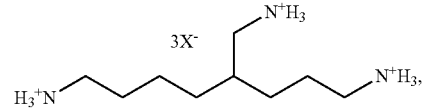
(IV)

one or more compounds of Formula (VI):

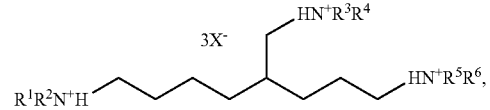
(VI)

one or more compounds of Formula (VII):

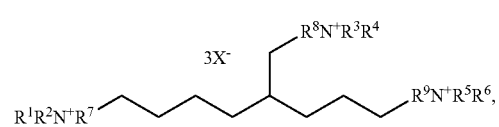
(VII)

or
mixtures thereof.

15. The method of claim 14, wherein, in the fracturing step:

the one compound of Formula (I) comprising 4-aminomethyl-1,8-octanediamine (TAN);
the one or more salts of Formula (II) comprising:
TAN formate salts,
methylated TAN formate salts,
TAN acetate salts,
TAN fumarate salts,
TAN citrate salts,
TAN oxalate salts,
TAN p-toluene sulfonate salts,
TAN methane sulfonate salts,
TAN aminotris(methylenephosphonic acid) salts,
TAN polyacrylate salts,
methylated TAN salts,
TAN benzyl quaternary salts,
TAN (±) epichlorohydrine quaternary salts,
TAN chloroethylether quaternary salts,
TAN diethyl sulfate quaternary salts,
TAN (±) epichlorohydrin salts, or
mixtures thereof;
the base fluid comprising:
aqueous base fluids comprising freshwater, production water, seawater, non-sodium brines, aqueous makeup systems, or mixture thereof; and
oil based fluids comprising synthetic hydrocarbon fluids, petroleum based hydrocarbon fluids, natural hydrocarbon fluids, or mixtures thereof.

16. The method of claim 15, wherein, in the fracturing step:

the one or more salts of Formula (III) comprising:
TAN formate salts,
TAN fumarate salts, TAN citrate salts,
TAN p-toluene sulfonate salts,
TAN methane sulfonate salts,
TAN aminotris(methylenephosphonic acid) salts,
TAN benzyl quaternary salts,
TAN (±) epichlorohydrine quaternary salts,
TAN chloroethylether quaternary salts,
TAN diethyl sulfate quaternary salts,
TAN (±) epichlorohydrin salts, or
mixtures thereof.

17. The method of claim 16, wherein, in the fracturing step:
the one or more salts of Formula (IV) comprising:
TAN formate salts,
TAN fumarate salts,
TAN citrate salts,
TAN p-toluene sulfonate salts,
TAN methane sulfonate salts,
TAN aminotris(methylenephosphonic acid) salts,
TAN benzyl quaternary salts,
TAN (±) epichlorohydrine quaternary salts,
TAN chloroethylether quaternary salts,
TAN diethyl sulfate quaternary salts,
TAN (±) epichlorohydrin salts, or
mixtures thereof.

18. The method of claim 17, wherein, in the fracturing step:
the one or more salts of Formula (V) comprising:
TAN formate salts,
TAN methane sulfonate salts,
TAN aminotris(methylenephosphonic acid) salts,
TAN diethyl sulfate quaternary salts, or
mixtures thereof.

* * * * *